(12) United States Patent
Kaneko et al.

(10) Patent No.: US 12,708,330 B2
(45) Date of Patent: Aug. 18, 2026

(54) MEDICAL IMAGE PROCESSING DEVICE, MEDICAL IMAGE PROCESSING METHOD, PROGRAM, AND IMAGE DIAGNOSTIC SYSTEM UTILIZING A SELECTION OF A TWO-DIMENSIONAL CANDIDATE IMAGE PREVIEW FOR IMAGING PARAMETER OPTIMIZATION

(71) Applicant: FUJIFILM Healthcare Corporation, Chiba (JP)

(72) Inventors: Yukio Kaneko, Tokyo (JP); Motohiro Tsuji, Chiba (JP); Tomoki Inoue, Tokyo (JP); Atsuro Suzuki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 190 days.

(21) Appl. No.: 18/755,684

(22) Filed: Jun. 27, 2024

(65) Prior Publication Data

US 2025/0025113 A1 Jan. 23, 2025

(30) Foreign Application Priority Data

Jul. 21, 2023 (JP) ................................ 2023-119293

(51) Int. Cl.
*A61B 5/00* (2006.01)
*A61B 5/055* (2006.01)
*G16H 30/40* (2018.01)

(52) U.S. Cl.
CPC .............. *A61B 5/748* (2013.01); *A61B 5/055* (2013.01); *A61B 5/7425* (2013.01); *G16H 30/40* (2018.01)

(58) Field of Classification Search
None
See application file for complete search history.

(56) References Cited

U.S. PATENT DOCUMENTS 5,539,426 A * 7/1996 Nishikawa .............. G06F 3/033 345/635
2017/0032090 A1 * 2/2017 Kamen .................. G06N 20/00

FOREIGN PATENT DOCUMENTS

| | | | |
|---|---|---|---|
| JP | H02260073 | | 10/1990 |
| JP | 2002183725 | A * | 6/2002 |
| JP | 2002183725 | X | 6/2002 |
| JP | 2003284705 | | 10/2003 |
| JP | 2003284705 | A * | 10/2003 |
| JP | 2019188031 | | 10/2019 |
| JP | 2019188031 | A * | 10/2019 |

* cited by examiner

*Primary Examiner* — Gabriel Mercado
(74) *Attorney, Agent, or Firm* — JCIPRNET

(57) ABSTRACT

A process of two-dimensionally disposing a plurality of candidate images obtained by performing image processing on medical imaging data by respectively combining a plurality of different candidate values of one image quality parameter type and a plurality of different candidate values of the other image quality parameter type such that the plurality of candidate images can be selected, and determining at least one of the candidate value of the one image quality parameter type or the candidate value of the other image quality parameter type corresponding to the selected candidate image, as a set value of the image quality parameter type is performed in an order of a high priority among three or more image quality parameter types.

15 Claims, 12 Drawing Sheets

FIG. 6

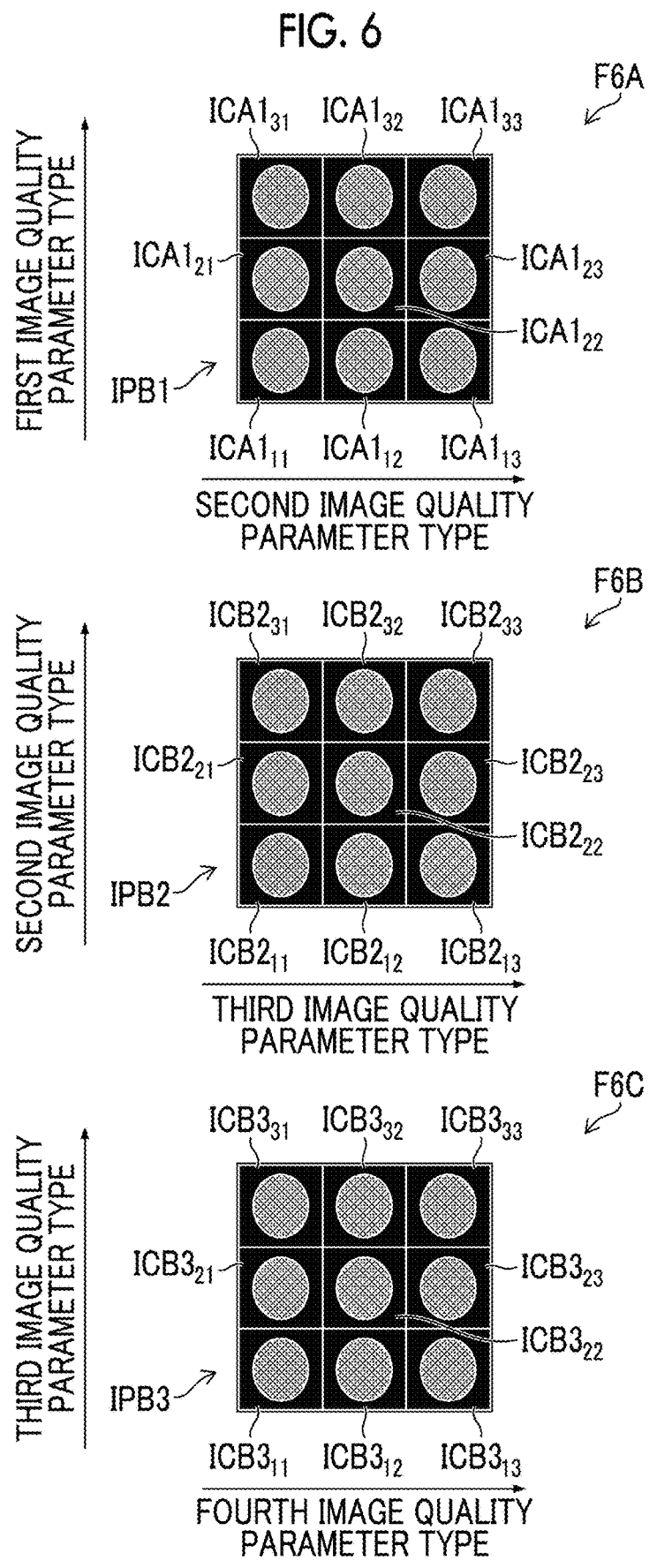

F6A $ICA1_{31}$ $ICA1_{32}$ $ICA1_{33}$ $ICA1_{21}$ $ICA1_{23}$ $ICA1_{22}$

IPB1

$ICA1_{11}$ $ICA1_{12}$ $ICA1_{13}$

FIRST IMAGE QUALITY PARAMETER TYPE

SECOND IMAGE QUALITY PARAMETER TYPE

F6B $ICB2_{31}$ $ICB2_{32}$ $ICB2_{33}$ $ICB2_{21}$ $ICB2_{23}$ $ICB2_{22}$

IPB2

$ICB2_{11}$ $ICB2_{12}$ $ICB2_{13}$

SECOND IMAGE QUALITY PARAMETER TYPE

THIRD IMAGE QUALITY PARAMETER TYPE

F6C $ICB3_{31}$ $ICB3_{32}$ $ICB3_{33}$ $ICB3_{21}$ $ICB3_{23}$ $ICB3_{22}$

IPB3

$ICB3_{11}$ $ICB3_{12}$ $ICB3_{13}$

THIRD IMAGE QUALITY PARAMETER TYPE

FOURTH IMAGE QUALITY PARAMETER TYPE

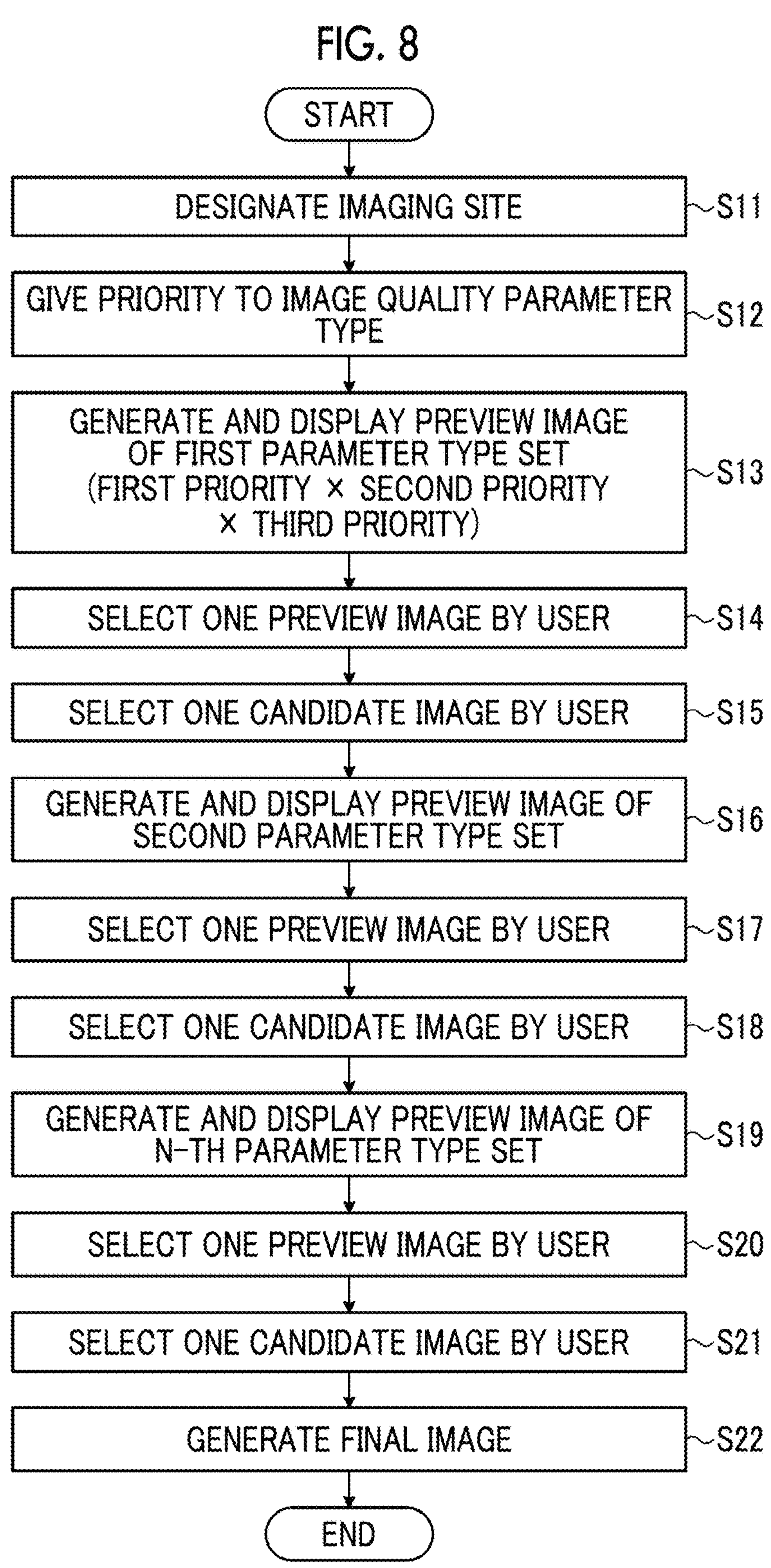
FIG. 8
START
DESIGNATE IMAGING SITE
S11
GIVE PRIORITY TO IMAGE QUALITY PARAMETER TYPE
S12
GENERATE AND DISPLAY PREVIEW IMAGE OF FIRST PARAMETER TYPE SET (FIRST PRIORITY × SECOND PRIORITY × THIRD PRIORITY)
S13
SELECT ONE PREVIEW IMAGE BY USER
S14
SELECT ONE CANDIDATE IMAGE BY USER
S15
GENERATE AND DISPLAY PREVIEW IMAGE OF SECOND PARAMETER TYPE SET
S16
SELECT ONE PREVIEW IMAGE BY USER
S17
SELECT ONE CANDIDATE IMAGE BY USER
S18
GENERATE AND DISPLAY PREVIEW IMAGE OF N-TH PARAMETER TYPE SET
S19
SELECT ONE PREVIEW IMAGE BY USER
S20
SELECT ONE CANDIDATE IMAGE BY USER
S21
GENERATE FINAL IMAGE
S22
END FIG. 12
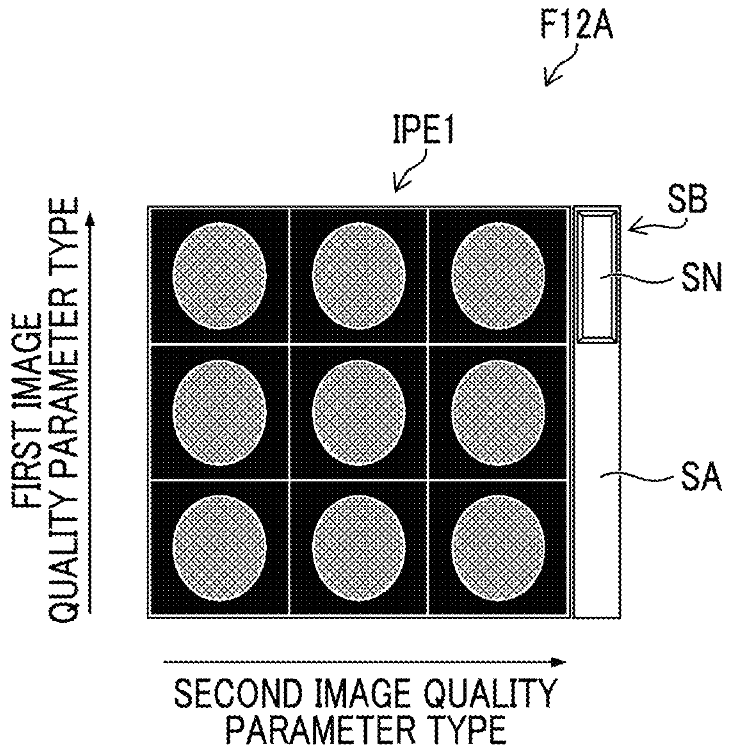
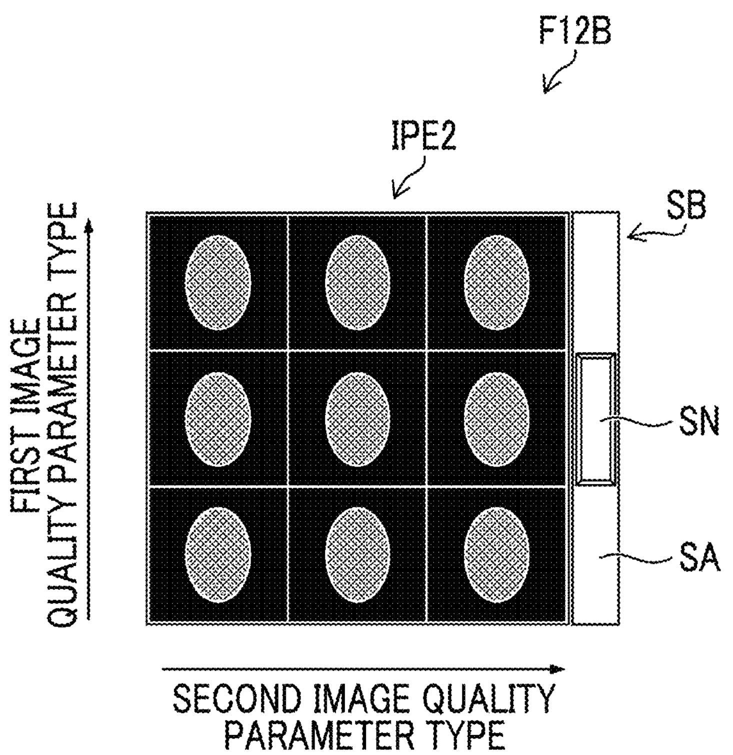

MEDICAL IMAGE PROCESSING DEVICE, MEDICAL IMAGE PROCESSING METHOD, PROGRAM, AND IMAGE DIAGNOSTIC SYSTEM UTILIZING A SELECTION OF A TWO-DIMENSIONAL CANDIDATE IMAGE PREVIEW FOR IMAGING PARAMETER OPTIMIZATION

CROSS-REFERENCE TO RELATED APPLICATION

The present application claims priority under 35 U.S.C § 119 (a) to Japanese Patent Application No. 2023-119293 filed on Jul. 21, 2023, which is hereby expressly incorporated by reference, in its entirety, into the present application.

BACKGROUND OF THE INVENTION

1. Field of the Invention

The present invention relates to a medical image processing device, a medical image processing method, a program, and an image diagnostic system, and particularly relates to a technique of determining a value of an image quality parameter type of a medical image.

2. Description of the Related Art

In a magnetic resonance imaging (MRI) image processing device, a user performs image processing after imaging to adjust an image quality. Such a parameter for adjusting the image quality needs to be changed for each patient and for each disease.

The parameter for adjusting the image quality is, for example, intensity of denoising processing. In addition, there is a demand for selecting an image quality preferred by the user in addition to the intensity of the denoising processing, but since there are too many parameter types for creating the image quality preferred by the user, it is difficult to adjust the value of the parameter type in a short time.

As a related art, a technique of displaying an image in which a value of each of two parameter types is changed and allowing the user to select the image while viewing the image is known (see JP2003-284705A, JP1990-260073A (JP-H2-260073A), and JP2019-188031A). In addition, a technique of extracting a preferred value of the parameter in advance by using the past image for three or more parameter types is known (see JP2002-183725A).

SUMMARY OF THE INVENTION

However, JP2003-284705A, JP1990-260073A (JP-H2-260073A), and JP2019-188031A do not disclose a method of selecting a value of each of three or more parameter types. As described above, there are a wide variety of parameter types, particularly in an MRI image, so that there is a problem that it is difficult to deal with the selection with the techniques disclosed in JP2003-284705A, JP1990-260073A (JP-H2-260073A), and JP2019-188031A.

In addition, JP2002-183725A does not disclose a method of adjusting the value of the parameter while viewing a newly captured image. Therefore, there is a problem that it is difficult to deal with an image of a rare case or the like that is not found in the past image.

The present invention has been made in view of such circumstances, and an object of the present invention is to provide a medical image processing device, a medical image processing method, a program, and an image diagnostic system capable of intuitively determining a value of each of three or more image quality parameter types of a medical image in a short time.

In order to achieve the above object, according to a first aspect of the present disclosure, there is provided a medical image processing device comprising: at least one processor; and at least one memory that stores an instruction to be executed by the processor, in which the processor acquires medical imaging data, displays, on a display device, a preview image in which, for a parameter type set of two image quality parameter types among three or more image quality parameter types related to an image quality of a medical image generated from the medical imaging data, a plurality of candidate images obtained by performing image processing on the medical imaging data by respectively combining a plurality of different candidate values of one image quality parameter type and a plurality of different candidate values of the other image quality parameter type are two-dimensionally disposed with the one image quality parameter type as one axis and the other image quality parameter type as the other axis, receives an operation of selecting one candidate image from the preview image, and determines at least one of the candidate value of the one image quality parameter type or the candidate value of the other image quality parameter type corresponding to the selected candidate image, as a set value of the image quality parameter type, the three or more image quality parameter types are each given a priority, after the set value is determined for a first parameter type set including a first image quality parameter type having a first priority and a second image quality parameter type having a second priority, the set value is determined for a second parameter type set different from the first parameter type set, and image processing is performed on the medical imaging data by applying the set value of each of the three or more image quality parameter types, to generate a medical image.

According to a medical image processing device according to a second aspect of the present disclosure, in the medical image processing device according to the first aspect, it is preferable that the processor determines the set value of the first image quality parameter type and the set value of the second image quality parameter type for the first parameter type set, and that the second parameter type set includes a third image quality parameter type having a third priority and a fourth image quality parameter type having a fourth priority.

According to a medical image processing device according to a third aspect of the present disclosure, in the medical image processing device according to the first aspect, it is preferable that the processor determines the set value of the first image quality parameter type for the first parameter type set, and that the second parameter type set includes the second image quality parameter type and a third image quality parameter type having a third priority.

According to a medical image processing device according to a fourth aspect of the present disclosure, in the medical image processing device according to the third aspect, it is preferable that a range of the plurality of candidate values of the second image quality parameter type of the second parameter type set is relatively narrower than a range of the plurality of candidate values of the second image quality parameter type of the first parameter type set, and includes the candidate value of the second image quality parameter type corresponding to the selected candidate image of the first parameter type set.

According to a medical image processing device according to a fifth aspect of the present disclosure, in the medical image processing device according to any one of the first to fourth aspects, it is preferable that the medical image processing device further comprises: a storage unit that holds the set values, which are determined in the past, of the three or more image quality parameter types, and that the processor relatively emphasizes a first candidate image corresponding to a combination of the set value, which is determined most frequently in the past, of the one image quality parameter type and the set value, which is determined most frequently in the past, of the other image quality parameter type over a second candidate image different from the first candidate image, in the preview image.

According to a medical image processing device according to a sixth aspect of the present disclosure, in the medical image processing device according to any one of the first to fifth aspects, it is preferable that the processor acquires an imaging site of the medical imaging data, and acquires the three or more image quality parameter types according to the imaging site.

According to a medical image processing device according to a seventh aspect of the present disclosure, in the medical image processing device according to any one of the first to sixth aspects, it is preferable that the priority is given relatively higher to the image quality parameter type of which a variation in the set value determined in the past is relatively large.

According to a medical image processing device according to an eighth aspect of the present disclosure, in the medical image processing device according to the first aspect or any one of the fifth to seventh aspects, it is preferable that the first parameter type set further includes a third image quality parameter type having a third priority, and that the processor displays, on the display device, a first preview image in which the plurality of candidate images having a first candidate value of the third image quality parameter type are two-dimensionally disposed among a plurality of candidate images obtained by performing image processing on the medical imaging data by respectively combining a plurality of different candidate values of the first image quality parameter type, a plurality of different candidate values of the second image quality parameter type, and a plurality of different candidate values of the third image quality parameter type, receives a switching operation for switching the candidate values of the third image quality parameter type, displays a second preview image in which the plurality of candidate images having a second candidate value, which is different from the first candidate value, of the third image quality parameter type are two-dimensionally disposed in accordance with the switching operation, receives an operation of selecting one candidate image from the first preview image or the second preview image, and determines at least the candidate value of the first image quality parameter type corresponding to the selected candidate image, as a set value of the first image quality parameter type.

According to a medical image processing device according to a ninth aspect of the present disclosure, in the medical image processing device according to the eighth aspect, it is preferable that the processor determines the candidate value of the second image quality parameter type corresponding to the selected candidate image as a set value of the second image quality parameter type, and determines the candidate value of the third image quality parameter type corresponding to the selected candidate image, as a set value of the third image quality parameter type.

According to a medical image processing device according to a tenth aspect of the present disclosure, in the medical image processing device according to any one of the first to ninth aspects, it is preferable that the candidate image is a three-dimensional image, and that the processor displays a third preview image in which slice images at first slice positions of the plurality of candidate images are two-dimensionally disposed, receives a switching operation for switching slice positions of the plurality of candidate images, displays a fourth preview image in which slice images at second slice positions different from the first slice positions are two-dimensionally disposed in accordance with the switching operation, and receives an operation of selecting one candidate image from the third preview image or the fourth preview image.

According to a medical image processing device according to an eleventh aspect of the present disclosure, in the medical image processing device according to any one of the first to tenth aspects, it is preferable that the processor performs image processing on the medical imaging data by applying the set value determined for the first parameter type set, to generate a plurality of candidate images of the second parameter type set.

In order to achieve the above object, according to a twelfth aspect of the present disclosure, there is provided an image diagnostic system comprising: the medical image processing device according to any one of the first to eleventh aspects; an image diagnostic apparatus that images the medical imaging data; the display device; and an input device for a user to perform an operation of selecting one candidate image from the preview image.

According to an image diagnostic system according to a thirteenth aspect of the present disclosure, in the image diagnostic system according to the twelfth aspect, it is preferable that the image diagnostic apparatus is a magnetic resonance imaging (MRI) apparatus.

In order to achieve the above object, according to a fourteenth aspect of the present disclosure, there is provided a medical image processing method comprising: via at least one processor, acquiring medical imaging data; displaying, on a display device, a preview image in which, for a parameter type set of two image quality parameter types among three or more image quality parameter types related to an image quality of a medical image generated from the medical imaging data, a plurality of candidate images obtained by performing image processing on the medical imaging data by respectively combining a plurality of different candidate values of one image quality parameter type and a plurality of different candidate values of the other image quality parameter type are two-dimensionally disposed with the one image quality parameter type as one axis and the other image quality parameter type as the other axis; receiving an operation of selecting one candidate image from the preview image; and determining at least one of the candidate value of the one image quality parameter type or the candidate value of the other image quality parameter type corresponding to the selected candidate image, as a set value of the image quality parameter type, in which the three or more image quality parameter types are each given a priority, after the set value is determined for a first parameter type set including a first image quality parameter type having a first priority and a second image quality parameter type having a second priority, the set value is determined for a second parameter type set different from the first parameter type set, and image processing is performed on the medical imaging data by applying the set value of each of the three or more image quality parameter types, to generate a medical image.

In order to achieve the above object, according to a fifteenth aspect of the present disclosure, there is provided a program for causing a computer to execute the medical image processing method according to the fourteenth aspect. The present disclosure also includes a non-transitory computer-readable recording medium, such as a compact disk-read only memory (CD-ROM), in which the program according to the fifteenth aspect is stored.

According to the present invention, it is possible to intuitively determine a value of each of the three or more image quality parameter types of the medical image in a short time.

BRIEF DESCRIPTION OF THE DRAWINGS

FIG. 6 is a diagram showing an example of a preview image.

FIG. 8 is a flowchart showing steps of the medical image processing method.

FIG. 12 is a diagram showing an example of a preview image.

DESCRIPTION OF THE PREFERRED EMBODIMENTS

Hereinafter, preferred embodiments of a medical image processing device, a medical image processing method, a program, and an image diagnostic system according to the present disclosure will be described with reference to the accompanying drawings.

Image Diagnostic System

Figure 1:
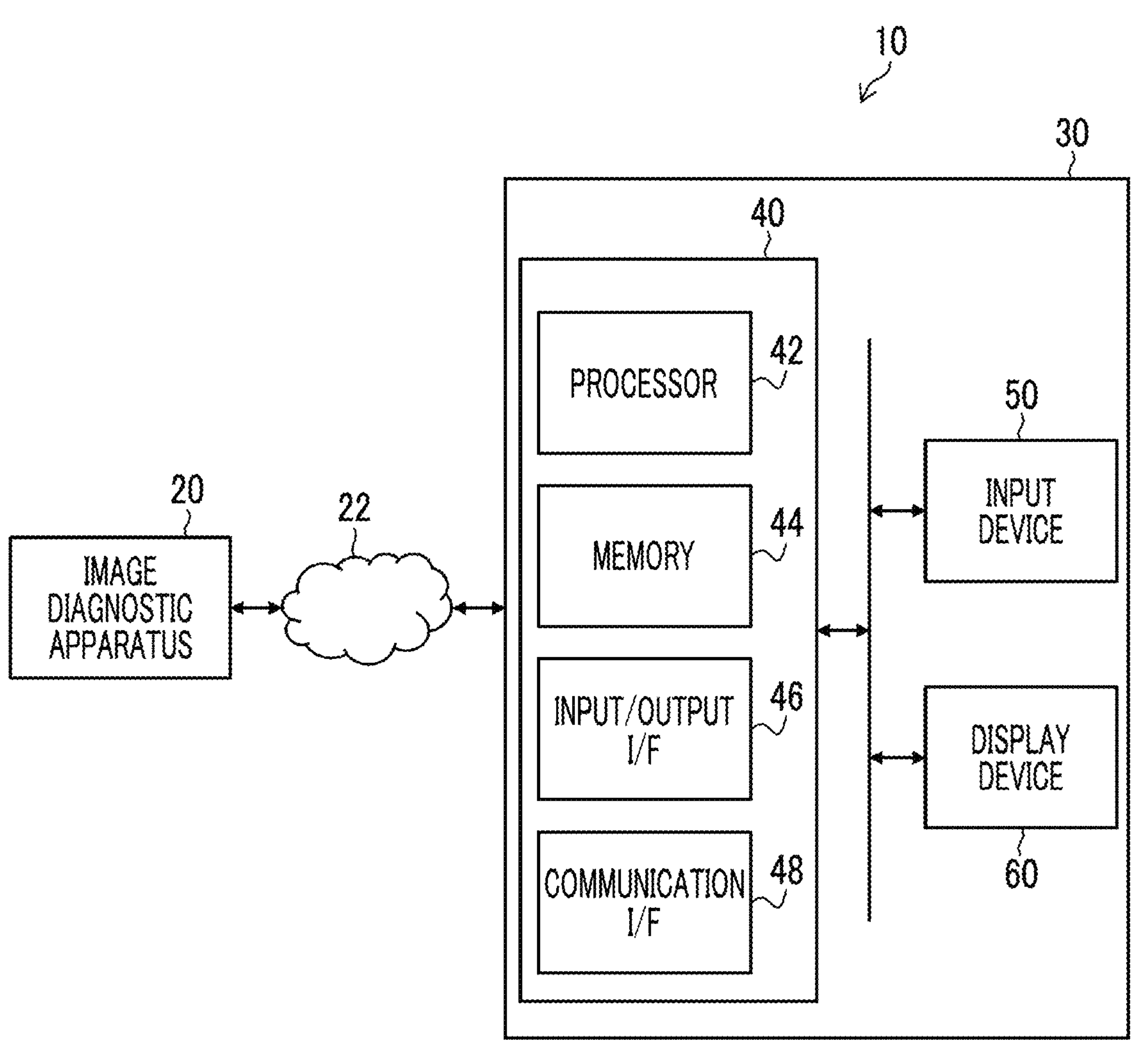
FIG. 1 is an overall configuration diagram of an image diagnostic system.

FIG. 1 is an overall configuration diagram of an image diagnostic system 10. As shown in FIG. 1, the image diagnostic system 10 is configured to comprise an image diagnostic apparatus 20 and an information processing apparatus 30.

The image diagnostic apparatus 20 and the information processing apparatus 30 are connected to each other via a network 22 such that data can be transmitted and received therebetween. The network 22 includes a wired or wireless local area network (LAN) that connects various devices in the medical institution in communication. The network 22 may include a wide area network (WAN) that connects the LANs of a plurality of medical institutions to each other.

The image diagnostic apparatus 20 includes an imaging apparatus that images an imaging site, which is a site of an examination target of a patient, and outputs medical imaging data. The image diagnostic apparatus 20 includes, for example, a computed tomography (CT) apparatus, a magnetic resonance imaging (MRI) apparatus, and a positron emission tomography (PET) apparatus.

The information processing apparatus 30 includes a medical image processing device 40, an input device 50, and a display device 60. The medical image processing device 40, the input device 50, and the display device 60 are connected to each other such that data can be transmitted and received therebetween.

The medical image processing device 40 is a device that generates a medical image by performing image processing applying a desired image quality parameter on the medical imaging data acquired from the image diagnostic apparatus 20. The medical image is, for example, a three-dimensional reconstructed image obtained by reconstructing the medical imaging data. The term "image" in the present specification includes not only the meaning of the image itself, such as a photograph, but also the meaning of image data which is a signal representing the image.

A personal computer or a workstation (an example of a "computer") is applied to the medical image processing device 40. The medical image processing device 40 comprises a processor 42, a memory 44, an input/output interface 46, and a communication interface 48.

The processor 42 executes an instruction stored in the memory 44. A hardware structure of the processor 42 is various processors as shown below. The various processors include a central processing unit (CPU) that is a general-purpose processor that executes software (program) to act as various functional units, a graphics processing unit (GPU) that is a processor specialized in image processing, a programmable logic device (PLD) that is a processor of which a circuit configuration can be changed after manufacture, such as a field programmable gate array (FPGA), and a dedicated electric circuit that is a processor having a circuit configuration designed for exclusive use in order to execute specific processing, such as an application specific integrated circuit (ASIC).

One processing unit may be configured of one of these various processors, or may be configured of two or more processors of the same type or different types (for example, a plurality of FPGAs, a combination of a CPU and an FPGA, or a combination of a CPU and a GPU). In addition, a plurality of functional units may be configured of one processor. As an example of configuring the plurality of functional units with one processor, first, there is a form in which, as typified by computers such as a client and a server, one processor is configured by combining one or more CPUs and software, and the processor functions as the plurality of processing units. Second, there is a form in which, as typified by a system on chip (SoC) and the like, a processor that implements functions of an entire system including the plurality of functional units with one integrated circuit (IC) chip is used. As described above, the various functional units are configured using one or more of the various processors as a hardware structure.

In addition, the hardware structure of these various processors is, more specifically, an electric circuit (circuitry) obtained by combining circuit elements such as semiconductor elements.

The memory 44 stores an instruction to be executed by the processor 42. The memory 44 includes a random access memory (RAM) and a read only memory (ROM) (both are not shown). The processor 42 executes software using various programs including a medical image processing program stored in the ROM, and executes various kinds of processing of the medical image processing device 40 by using a parameter stored in the ROM and the like, with the RAM as a work region.

The input/output interface 46 controls an input from the input device 50 and an output to the display device 60.

The communication interface 48 controls a communication with the image diagnostic apparatus 20 via the network 22 in accordance with a predetermined protocol.

The medical image processing device 40 may be included in the image diagnostic apparatus 20. In addition, the medical image processing device 40 may be a cloud server accessible from a plurality of medical institutions via the Internet. The processing performed by the medical image processing device 40 may be a cloud service based on a charge system or a fixed fee system.

The input device 50 includes a mouse (not shown) and a keyboard (not shown). A user inputs an instruction to the medical image processing device 40 by using the input device 50.

The display device 60 includes a liquid crystal display, an organic electro luminescence (EL) display, a plasma display, or a projector. The display device 60 displays a medical image or the like in response to a command from the medical image processing device 40.

The information processing apparatus 30 may comprise a touch panel display in which the input device 50 and the display device 60 are integrated.

Functional Configuration of Medical Image Processing Device

Figure 2:
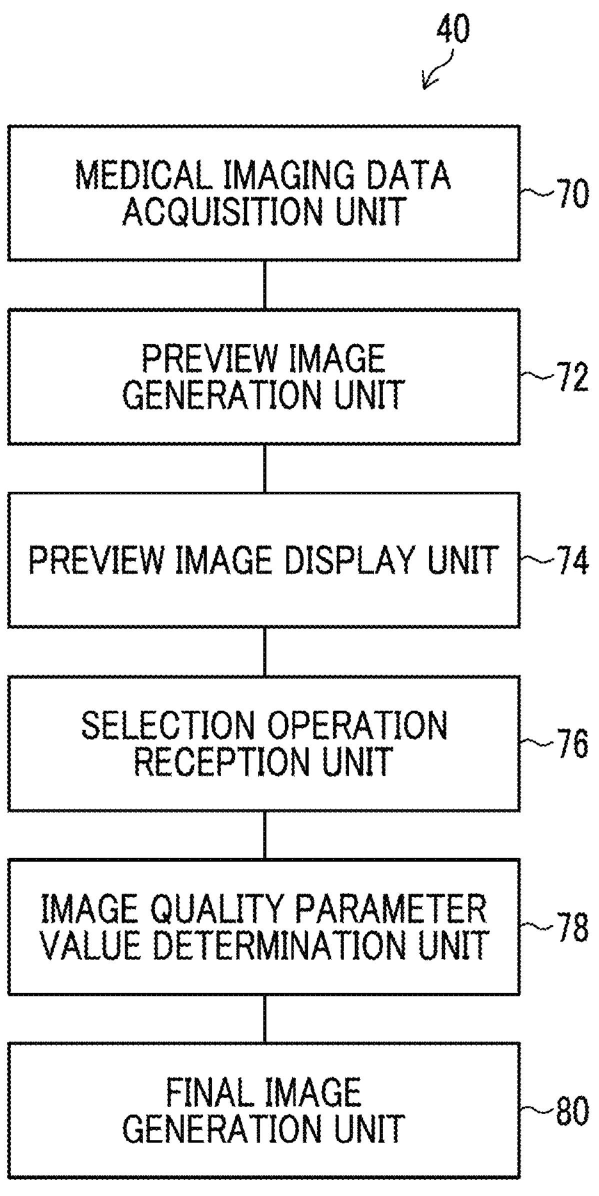
FIG. 2 is a block diagram showing a functional configuration of a medical image processing device.

FIG. 2 is a block diagram showing a functional configuration of the medical image processing device 40. Each function of the medical image processing device 40 is realized by the processor 42 executing the medical image processing program stored in the memory 44. As shown in FIG. 2, the medical image processing device 40 comprises a medical imaging data acquisition unit 70, a preview image generation unit 72, a preview image display unit 74, a selection operation reception unit 76, an image quality parameter value determination unit 78, and a final image generation unit 80.

The medical imaging data acquisition unit 70 acquires the medical imaging data from the image diagnostic apparatus 20 via the network 22. The medical imaging data includes, for example, magnetic resonance data imaged by the MRI apparatus and projection data imaged by the CT apparatus.

The preview image generation unit 72 generates a preview image for determining a set value of an image quality parameter type, which is related to an image quality of a medical image generated from the medical imaging data and is a post-processing parameter to be applied to the medical imaging data.

The image quality parameter type includes "S/N ratio (denoising intensity)", "edge emphasis intensity", "contrast", and "spatial resolution". The image quality parameter type may include "Truncation", "Shading", "Mode", "Correction", "Strength", "T2 correct.", "Adaptive Filter", "Edge Enhance", "DLR Level", "MIP Image", "D.C. Level", "Region Cut", "W-Width1", and "W-Level1". The image quality parameter type is stored in the memory 44.

The preview image generation unit 72 prepares, for a parameter type set including two image quality parameter types among three or more image quality parameter types, a plurality of different candidate values of one image quality parameter type and a plurality of different candidate values of the other image quality parameter type, and performs image processing on the medical imaging data by combining the plurality of different candidate values of both image quality parameter types, to generate a plurality of candidate images. Further, the preview image generation unit 72 generates a preview image in which the plurality of candidate images are two-dimensionally disposed with the one image quality parameter as one axis and the other image quality parameter as the other axis.

The preview image display unit 74 displays the preview image generated by the preview image generation unit 72 on the display device 60 such that the user can select one candidate image. The user can select one candidate image from the preview image using the input device 50. The selection operation reception unit 76 receives an operation of selecting one candidate image from the input device 50.

The image quality parameter value determination unit 78 determines at least one of the candidate value of the one image quality parameter type or a candidate value of the type of the other image quality parameter corresponding to the selected candidate image, as a set value of the image quality parameter type. The image quality parameter value determination unit 78 may store the set value of the determined image quality parameter type in the memory 44.

The final image generation unit 80 performs image processing on the medical imaging data by applying the set value of each of the three or more image quality parameter types, to generate a medical image that is a final image. The final image generation unit 80 may display the generated final image on the display device 60, or may store the generated final image in a medical image database (not shown).

Medical Image Processing Method: First Embodiment

Figure 3:
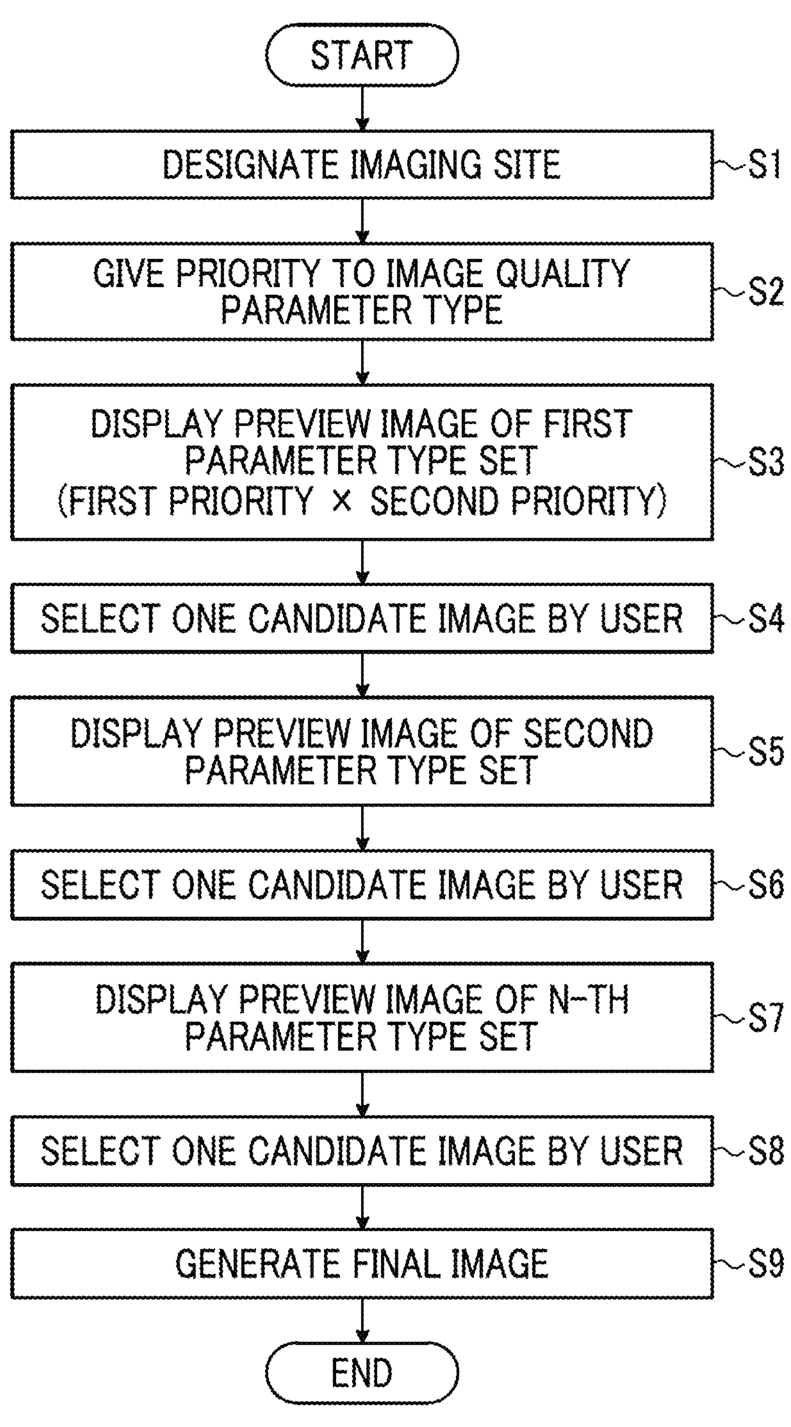
FIG. 3 is a flowchart showing steps of a medical image processing method.

FIG. 3 is a flowchart showing steps of a medical image processing method according to a first embodiment performed by the medical image processing device 40. The medical image processing method is a method of allowing the user such as a doctor to determine the set value of each of the three or more image quality parameter types in a short time. The medical image processing method is realized by the processor 42 executing the medical image processing program stored in the memory 44. The medical image processing program may be provided by a computer-readable non-transitory storage medium, or may be provided via the Internet.

In step S1, the user designates an imaging site by using the input device 50. The imaging site includes, for example, at least one of "head", "abdomen", or "joint".

In step S2, the user uses the input device 50 to select in advance three or more important image quality parameter types from among the image quality parameter types stored in the memory 44, and gives a non-overlapping priority to each of the selected image quality parameter types.

For example, in a case where the imaging site is "head" and the user wants to diagnose a fine tissue structure in the brain, the user may set a first priority as "spatial resolution", a second priority as "S/N ratio (denoising intensity)", a third priority as "edge emphasis intensity", and a fourth priority as "contrast".

In addition, in a case where the imaging site is "abdomen" and the user wants to make a difference between a diseased part and a normal tissue clearly visible in a case of a contrast examination of the liver, the user may set a first priority as "contrast", a second priority as "edge emphasis intensity", a third priority as "S/N ratio (denoising intensity)", and a fourth priority as "spatial resolution".

Further, in a case where the imaging site is "joint" and the user wants to accurately measure a dimension of a thickness of the cartilage of the knee joint, the user may set a first priority as "spatial resolution", a second priority as "edge emphasis intensity", a third priority as "S/N ratio (denoising intensity)", and a fourth priority as "contrast".

Here, the four image quality parameter types are selected in each imaging site, but the user need only select at least three image quality parameter types and give priorities. In addition, the user may select five or more image quality parameter types and give priorities.

The medical image processing device 40 may store the image quality parameter types and the priority of each image quality parameter type according to the imaging site selected in step S2, in the memory 44.

The medical image processing device 40 may store the priorities according to the imaging site in the memory 44 or the like in advance. In this case, in step S2, the medical image processing device 40 need only read out the priorities according to the imaging site designated in step S1.

Subsequently, the medical imaging data acquisition unit 70 acquires medical imaging data of the imaging site designated in step S1. The preview image generation unit 72 generates a preview image of a first parameter type set.

Figure 4:
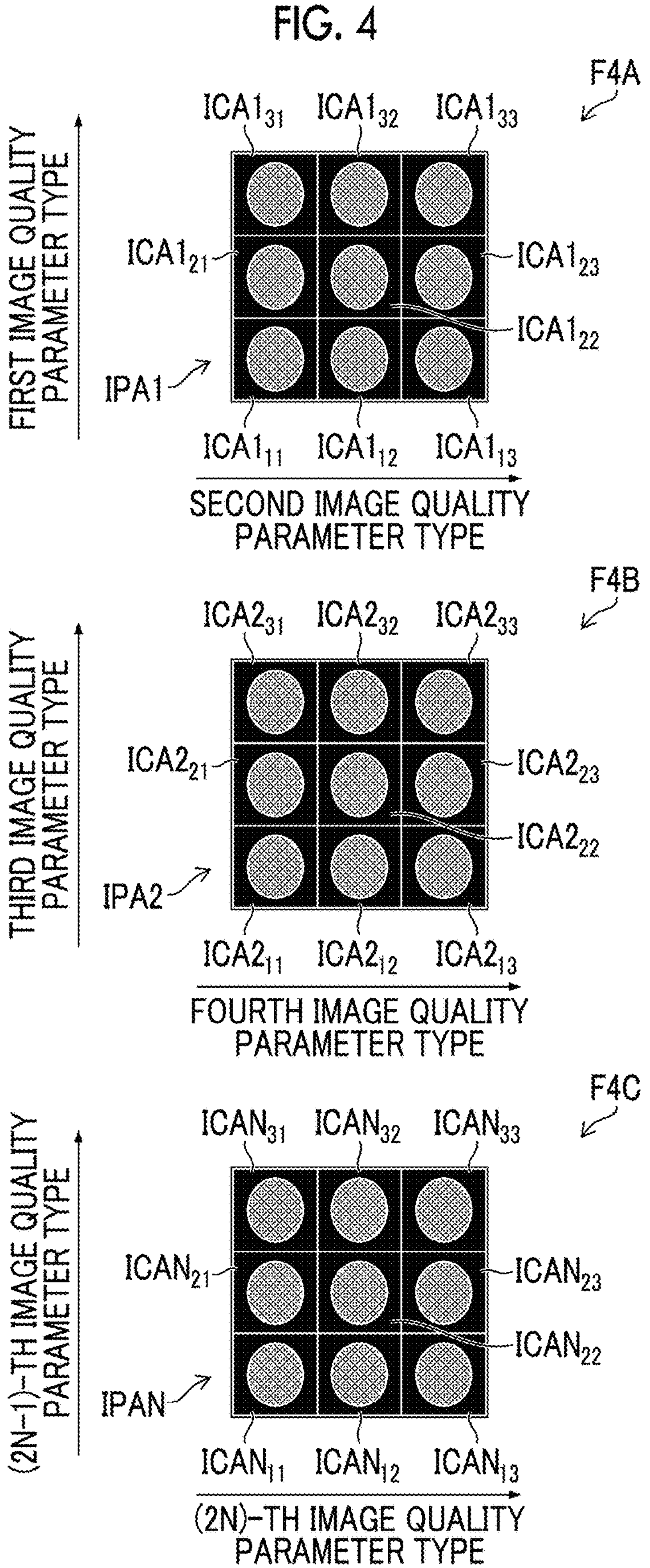
FIG. 4 is a diagram showing an example of a preview image.

Further, in step S3, the preview image display unit 74 displays the preview image of the first parameter type set, on the display device 60. FIG. 4 is a diagram showing an example of the preview image displayed on the display device 60. F4A in FIG. 4 shows a preview image IPA1 displayed in step S3.

The first parameter type set includes a first image quality parameter type having a first priority and a second image quality parameter type having a second priority among three or more image quality parameter types acquired according to the imaging site. In a case where the imaging site is "head", the first image quality parameter type is "spatial resolution", and the second image quality parameter type is "S/N ratio (denoising intensity)".

The first image quality parameter type has candidate values that are values of a plurality of different first image quality parameters, and the second image quality parameter type has candidate values that are values of a plurality of different second image quality parameters. Here, it is assumed that the first image quality parameter type has three candidate values P1A, P1B, and P1C, and the second image quality parameter type has three candidate values P2A, P2B, and P2C. The candidate value is not limited to a numerical value, and the presence or absence of selection of whether or not to use the image quality parameter in the image processing may be included.

The preview image generation unit 72 performs image processing on the medical imaging data for each of combinations of the respective candidate values of the first image quality parameter type and the respective candidate values of the second image quality parameter type, that is, for each of nine combinations of P1A×P2A, P1A×P2B, P1A×P2C, P1B×P2A, P1B×P2B, P1B×P2C, P1C×P2A, P1C×P2B, and P1C×P2C, to generate nine candidate images $ICA1_{11}$, $ICA1_{12}$, $ICA1_{13}$, $ICA1_{21}$, $ICA1_{22}$, $ICA1_{23}$, $ICA1_{31}$, $ICA1_{32}$, and $ICA1_{33}$.

For the image quality parameter type other than the first image quality parameter type and the second image quality parameter type, the preview image generation unit 72 need only perform the image processing using a predetermined fixed value.

Further, the preview image generation unit 72 generates a preview image IPA1 in which the nine candidate images $ICA1_{11}$, $ICA1_{12}$, $ICA1_{13}$, $ICA1_{21}$, $ICA1_{22}$, $ICA1_{23}$, $ICA1_{31}$, $ICA1_{32}$, and $ICA1_{33}$ are two-dimensionally disposed with the first image quality parameter type as a vertical axis and the second image quality parameter type as a horizontal axis. In a case where the candidate images $ICA1_{11}$, $ICA1_{12}$, $ICA1_{13}$, $ICA1_{21}$, $ICA1_{22}$, $ICA1_{23}$, $ICA1_{31}$, $ICA1_{32}$, and $ICA1_{33}$ are three-dimensional images, the preview image generation unit 72 need only two-dimensionally dispose slice images in the same direction and at the same slice position.

In the example shown in F4A, the candidate images $ICA1_{31}$, $ICA1_{32}$, and $ICA1_{33}$ disposed in order from the left in an upper row of the preview image IPA1 are images in which the value of the first image quality parameter type is the candidate value P1C and the values of the second image quality parameter type are the candidate values P2A, P2B, and P2C. In addition, the candidate images $ICA1_{31}$, $ICA1_{21}$, and $ICA1_{11}$ disposed in order from the top on a left side of the preview image IPA1 are images in which the values of the first image quality parameter type are the candidate values P1C, P1B, and P1A and the value of the second image quality parameter type is the candidate value P2A.

Figure 5:
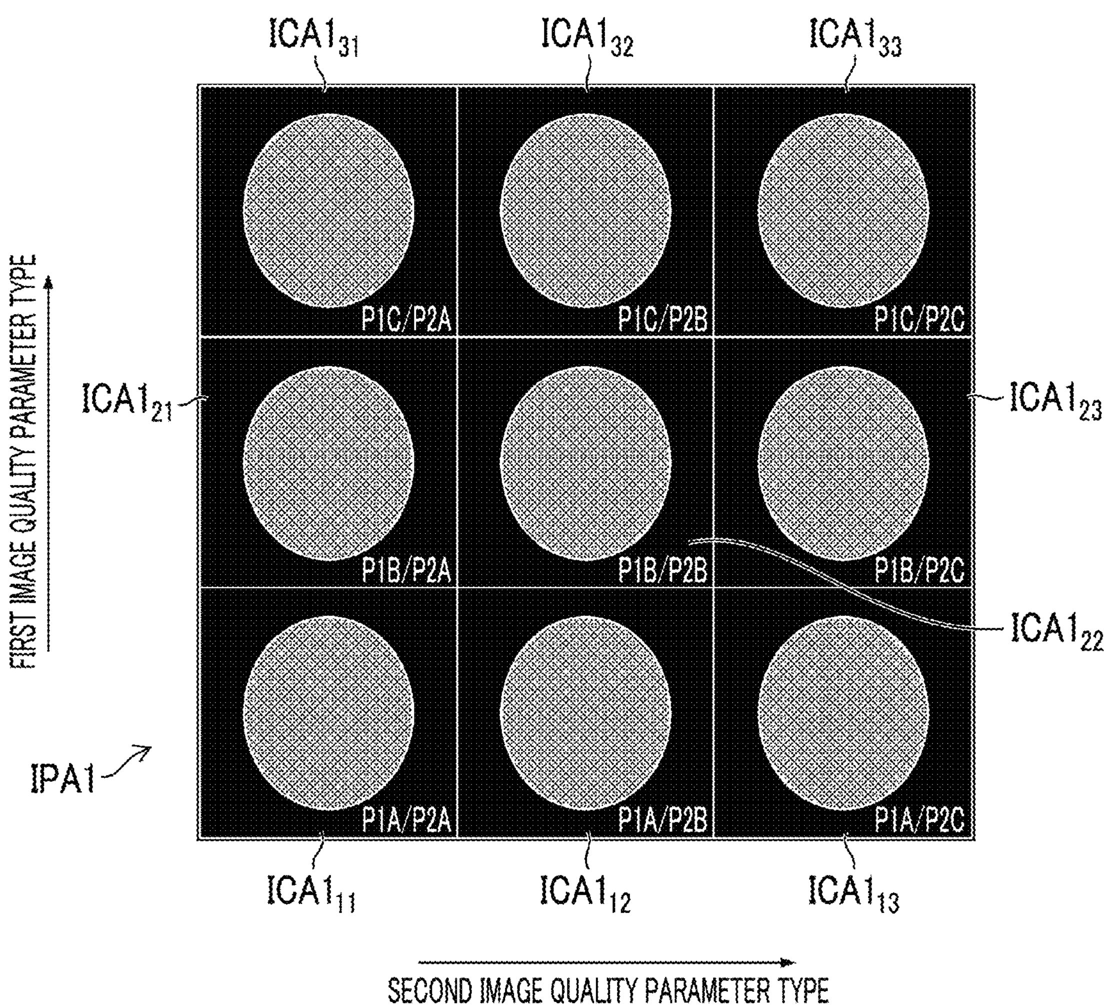
FIG. 5 is a diagram showing another example of the preview image.

The preview image may display the value of the image quality parameter type of each candidate image. FIG. 5 is a diagram showing another example of the preview image IPA1. In the preview image IPA1 shown in FIG. 5, the value of the first image quality parameter type and the value of the second image quality parameter type are displayed at a corner of each of the nine candidate images $ICA1_{11}$, $ICA1_{12}$, $ICA1_{13}$, $ICA1_{21}$, $ICA1_{22}$, $ICA1_{23}$, $ICA1_{31}$, $ICA1_{32}$, and $ICA1_{33}$. For example, at a corner of the candidate image $ICA1_{31}$, a character "P1C/P2A" indicating that the value of the first image quality parameter type and the value of the second image quality parameter type of the candidate image $ICA1_{31}$ are respectively the candidate value P1C and candidate value P2A is displayed.

Returning to the description of FIG. 3, in step S4, the user uses the input device 50 to select one candidate image among the nine candidate images $ICA1_{11}$, $ICA1_{12}$, $ICA1_{13}$, $ICA1_{21}$, $ICA1_{22}$, $ICA1_{23}$, $ICA1_{31}$, $ICA1_{32}$, and $ICA1_{33}$ of the preview image IPA1. The selection operation reception unit 76 receives the operation of selecting the candidate image.

The image quality parameter value determination unit 78 determines the candidate value of the first image quality parameter type corresponding to the candidate image selected in step S4, as a set value of the first image quality parameter type. In addition, the image quality parameter value determination unit 78 determines the candidate value of the second image quality parameter type corresponding to the candidate image selected in step S4, as a set value of the second image quality parameter type. For example, in a case where the selected candidate image is the candidate image $ICA1_{11}$, the set value of the first image quality parameter type is determined to be P1A, and the set value of the second image quality parameter type is determined to be P2A. In addition, in a case where the selected candidate image is the candidate image $ICA1_{23}$, the set value of the first image quality parameter type is determined to be P1B, and the set value of the second image quality parameter type is determined to be P2C.

Subsequently, the preview image generation unit 72 generates a preview image of a second parameter type set. In step S5, the preview image display unit 74 displays the preview image of the second parameter type set, on the display device 60. F4B in FIG. 4 shows a preview image IPA2 displayed in step S5.

The second parameter type set includes a third image quality parameter type having a third priority and a fourth image quality parameter type having a fourth priority. In a case where the imaging site is "head", the third image quality parameter type is "edge emphasis intensity", and the fourth image quality parameter type is "contrast". Here, it is assumed that the third image quality parameter type has three candidate values P3A, P3B, and P3C, and the fourth image quality parameter type has three candidate values P4A, P4B, and P4C.

The preview image generation unit 72 performs image processing on the medical imaging data for each of combinations of the respective candidate values of the third image quality parameter type and the respective candidate values of the fourth image quality parameter type, that is, for each of nine combinations of P3A×P4A, P3A×P4B, P3A×P4C, P3B×P4A, P3B×P4B, P3B×P4C, P3C×P4A, P3C×P4B, and P3C×P4C, to generate nine candidate images $ICA2_{11}$, $ICA2_{12}$, $ICA2_{13}$, $ICA2_{21}$, $ICA2_{22}$, $ICA2_{23}$, $ICA2_{31}$, $ICA2_{32}$, and $ICA2_{33}$. For the third parameter type and the fourth parameter type in the image processing in step S5, the preview image generation unit 72 may use the set values determined in step S4.

Further, the preview image generation unit 72 generates a preview image IPA2 in which the nine candidate images $ICA2_{11}$, $ICA2_{12}$, $ICA2_{13}$, $ICA2_{21}$, $ICA2_{22}$, $ICA2_{23}$, $ICA2_{31}$, $ICA2_{32}$, and $ICA2_{33}$ are two-dimensionally disposed with the third image quality parameter type as a vertical axis and the fourth image quality parameter type as a horizontal axis.

In step S6, the user uses the input device 50 to select one candidate image among the nine candidate images $ICA2_{11}$, $ICA2_{12}$, $ICA2_{13}$, $ICA2_{21}$, $ICA2_{22}$, $ICA2_{23}$, $ICA2_{31}$, $ICA2_{32}$, and $ICA2_{33}$ of the preview image IPA2. The selection operation reception unit 76 receives the operation of selecting the candidate image.

The image quality parameter value determination unit 78 determines the candidate value of the third image quality parameter type corresponding to the candidate image selected in step S6, as a set value of the third image quality parameter type. In addition, the image quality parameter value determination unit 78 determines the candidate value of the fourth image quality parameter type corresponding to the candidate image selected in step S6, as a set value of the fourth image quality parameter type.

In this way, for the three or more image quality parameter types acquired according to the imaging site, the set values are sequentially determined for each image quality parameter type in the parameter type set consisting of two image quality parameter types combined in descending order of the priority.

Further, the preview image generation unit 72 generates a preview image of a (N)-th parameter type set. In step S7, the preview image display unit 74 displays the preview image of the (N)-th parameter type set, on the display device 60. F4C in FIG. 4 shows a preview image IPAN displayed in step S7.

The (N)-th parameter type set includes a (2N−1)-th image quality parameter type having a (2N−1)-th priority and a (2N)-th image quality parameter type having a (2N)-th priority. Here, it is assumed that the (2N−1)-th image quality parameter type has three candidate values P(2N−1)A, P(2N−1)B, and P(2N−1)C, and the (2N)-th image quality parameter type has three candidate values P(2N)A, P(2N)B, and P(2N) C.

The preview image generation unit 72 performs image processing on the medical imaging data for each of combinations of the respective candidate values of the (2N−1)-th image quality parameter type and the respective candidate values of the (2N)-th image quality parameter type, that is, for each of nine combinations of P(2N−1)A×P(2N)A, P(2N−1)A× P(2N)B, P(2N−1)A×P(2N)C, P(2N−1)B×P(2N)A, P(2N−1)B×P(2N)B, P(2N−1)B×P(2N)C, P(2N−1)C×P(2N)A, P(2N−1)C×P(2N)B, and P(2N−1)C×P(2N)C, to generate nine candidate images $ICAN_{11}$, $ICAN_{12}$, $ICAN_{13}$, $ICAN_{21}$, $ICAN_{22}$, $ICAN_{23}$, $ICAN_{31}$, $ICAN_{32}$, and $ICAN_{33}$. For the first image quality parameter type to the (2N−2)-th image quality parameter type in the image processing in step S7, the preview image generation unit 72 may use the set values determined so far.

Further, the preview image generation unit 72 generates a preview image IPAN in which the nine candidate images $ICAN_{11}$, $ICAN_{12}$, $ICAN_{13}$, $ICAN_{21}$, $ICAN_{22}$, $ICAN_{23}$, $ICAN_{31}$, $ICAN_{32}$, and $ICAN_{33}$ are two-dimensionally disposed with the (2N−1)-th image quality parameter type as a vertical axis and the (2N)-th image quality parameter type as a horizontal axis.

In step S8, the user uses the input device 50 to select one candidate image among the nine candidate images $ICAN_{11}$, $ICAN_{12}$, $ICAN_{13}$, $ICAN_{21}$, $ICAN_{22}$, $ICAN_{23}$, $ICAN_{31}$, $ICAN_{32}$, and $ICAN_{33}$ of the preview image IPAN. The selection operation reception unit 76 receives the operation of selecting the candidate image.

The image quality parameter value determination unit 78 determines the candidate value of the (2N−1)-th image quality parameter type corresponding to the candidate image selected in step S8, as a set value of the (2N−1)-th image quality parameter type. In addition, the image quality parameter value determination unit 78 determines the candidate value of the (2N)-th image quality parameter type corresponding to the candidate image selected in step S8, as a set value of the (2N)-th image quality parameter type.

Finally, in step S9, the final image generation unit 80 performs image processing on the acquired medical imaging data by applying the set value of each of the first to (2N)-th image quality parameter types, to generate a medical image that is a final image.

In a case where the number of the three or more image quality parameter types acquired according to the imaging site is the odd number, for an image quality parameter type having a lowest priority, the medical imaging data need only be subjected to the image processing using a plurality of candidate values of the image quality parameter type to generate a plurality of candidate images, a preview image in which the plurality of candidate images are one-dimensionally disposed need only be generated, and any one of the candidate images need only be selected by the user.

According to the present embodiment, the user can intuitively check which candidate value combination of the candidate image is preferable for the image quality in each image quality parameter type set by checking the preview image displayed on the display device 60, so that the user can select an appropriate value for each image quality parameter type.

Here, although the example has been described in which the number of the candidate values of each image quality parameter type is three, the number of the candidate values is not limited to three. Assuming that L and M are each an integer of two or more, the preview image generation unit 72 can generate a preview image in which (L×M) types of candidate images obtained by combining L candidate values of one image quality parameter type and M candidate values of the other image quality parameter type are disposed. L and M may be different for each image quality parameter type set. In addition, in a case where the candidate images are two-dimensionally disposed, which image quality parameter type is disposed on the vertical axis or on the horizontal axis may be randomly determined.

In addition, the number of the candidate values of each image quality parameter type may be fixed to three, and the three candidate values may be configured to be changeable to a desired value by a user.

Here, the three or more image quality parameter types are given non-overlapping priorities, but the priorities may partially overlap. For example, the first parameter type set may include a first image quality parameter type having a first priority and a second image quality parameter type having the same first priority as the first image quality parameter type.

Second Embodiment

An image processing method according to a second embodiment will be described with reference to the flowchart of FIG. 3, focusing on parts different from the first embodiment. In the first embodiment, the three or more image quality parameter types acquired according to the imaging site are allocated to the parameter type sets without overlapping, but in the second embodiment, one image quality parameter type may be overlappingly selected for a plurality of parameter type sets.

The processing of step S1 and step S2 is the same as that of the first embodiment. In step S3, the preview image display unit 74 displays the preview image of the first parameter type set, on the display device 60. The first parameter type set includes a first image quality parameter type having a first priority and a second image quality parameter type having a second priority.

FIG. 6 is a diagram showing an example of the preview image displayed on the display device 60. F6A in FIG. 6 shows a preview image IPB1 displayed in step S3. The preview image IPB1 is the same image as the preview image IPA1 in the first embodiment. That is, the nine candidate images $ICA1_{11}$, $ICA1_{12}$, $ICA1_{13}$, $ICA1_{21}$, $ICA1_{22}$, $ICA1_{23}$, $ICA1_{31}$, $ICA1_{32}$, and $ICA1_{33}$ included in the preview image IPB1 are images obtained by performing the image processing on the combination of the three candidate values P1A, P1B, and P1C of the first image quality parameter type and the three candidate values P2A, P2B, and P2C of the second image quality parameter type.

In step S4, the user uses the input device 50 to select one candidate image among the nine candidate images $ICA1_{11}$, $ICA1_{12}$, $ICA1_{13}$, $ICA1_{21}$, $ICA1_{22}$, $ICA1_{23}$, $ICA1_{31}$, $ICA1_{32}$, and $ICA1_{33}$ of the preview image IPB1. The selection operation reception unit 76 receives the operation of selecting the candidate image.

The image quality parameter value determination unit 78 determines the candidate value of the first image quality parameter type corresponding to the candidate image selected in step S4, as a set value of the first image quality parameter type. For example, in a case where the selected candidate image is the candidate image $ICA1_{21}$, the set value of the first image quality parameter type is determined to be P1B. In addition, in a case where the selected candidate image is the candidate image $ICA1_{33}$, the set value of the first image quality parameter type is determined to be P1C. The set value of the second image quality parameter type is not determined at this point.

Next, in step S5, the preview image display unit 74 displays the preview image of the second parameter type set, on the display device 60. F6B in FIG. 6 shows a preview image IPB2 displayed in step S5.

In the second embodiment, the second parameter type set includes a second image quality parameter and a third image quality parameter type having a third priority. Here, it is assumed that the second image quality parameter type has three candidate values P2D, P2E, and P2F, and the third image quality parameter type has three candidate values P3A, P3B, and P3C.

Here, it is preferable that a range of the plurality of candidate values of the second image quality parameter type of the second parameter type set is relatively narrower than a range of the plurality of candidate values of the second image quality parameter type of the first parameter type set. That is, assuming that $P2A<P2B<P2C$ and $P2D<P2E<P2F$, it is preferable that a relationship of $(P2C-P2A)>(P2F-P2D)$ is satisfied.

In addition, it is preferable that the range of the plurality of candidate values of the second image quality parameter type of the second parameter type set includes the candidate value of the second image quality parameter type corresponding to the candidate image of the first parameter type set selected in step S4. That is, assuming that the candidate value of the second image quality parameter type corresponding to the candidate image selected in step S4 is P2Z, it is preferable that a relationship of $P2D \leq P2Z \leq P2F$ is satisfied.

The number of the plurality of candidate values of the second image quality parameter type of the second parameter type set may be relatively smaller than the number of the plurality of candidate values of the second image quality parameter type of the first parameter type set.

The preview image generation unit 72 performs image processing on the medical imaging data for each of combinations of the respective candidate values of the second image quality parameter type and the respective candidate values of the third image quality parameter type, that is, for each of nine combinations of P2D×P3A, P2D×P3B, P2D×P3C, P2E×P3A, P2E×P3B, P2E×P3C, P2F×P3A, P2F×P3B, and P2F×P3C, to generate nine candidate images $ICB2_{11}$, $ICB2_{12}$, $ICB2_{13}$, $ICB2_{21}$, $ICB2_{22}$, $ICB2_{23}$, $ICB2_{31}$, $ICB2_{32}$, and $ICB2_{33}$.

Further, the preview image generation unit 72 generates a preview image IPB2 in which the nine candidate images $ICB2_{11}$, $ICB2_{12}$, $ICB2_{13}$, $ICB2_{21}$, $ICB2_{22}$, $ICB2_{23}$, $ICB2_{31}$, $ICB2_{32}$, and $ICB2_{33}$ are two-dimensionally disposed with the second image quality parameter type as a vertical axis and the third image quality parameter type as a horizontal axis. In the preview image IPB2, the second image quality parameter type may be used as a horizontal axis, and the third image quality parameter type may be used as a vertical axis.

In step S6, the user uses the input device 50 to select one candidate image among the nine candidate images $ICB2_{11}$, $ICB2_{12}$, $ICB2_{13}$, $ICB2_{21}$, $ICB2_{22}$, $ICB2_{23}$, $ICB2_{31}$, $ICB2_{32}$, and $ICB2_{33}$ of the preview image IPB2. The selection operation reception unit 76 receives the operation of selecting the candidate image.

The image quality parameter value determination unit 78 determines the candidate value of the second image quality parameter type corresponding to the candidate image selected in step S6, as a set value of the second image quality parameter type. The set value of the third image quality parameter type is not determined at this point.

Subsequently, the preview image display unit 74 displays the preview image of the third parameter type set, on the display device 60. F6C in FIG. 6 shows a preview image IPB3.

The third parameter type set includes a third image quality parameter and a fourth image quality parameter type having a fourth priority. It is assumed that the third image quality parameter type has three candidate values P3D, P3E, and P3F, and the fourth image quality parameter type has three candidate values P4A, P4B, and P4C. As in the second parameter type set, assuming that $P3A<P3B<P3C$ and $P3D<P3E<P3F$, it is preferable that a relationship of $(P3C-P3A)>(P3F-P3D)$ is satisfied. In addition, assuming that the candidate value of the third image quality parameter type corresponding to the candidate image selected in step S6 is P3Z, it is preferable that a relationship of $P3D \leq P3Z \leq P3F$ is satisfied.

The preview image generation unit 72 performs image processing on the medical imaging data for each of combinations of the respective candidate values of the third image quality parameter type and the respective candidate values of the fourth image quality parameter type, that is, for each of nine combinations of P3D×P4A, P3D×P4B, P3D×P4C, P3E×P4A, P3E×P4B, P3E×P4C, P3F×P4A, P3F×P4B, and P3F×P4C, to generate nine candidate images $ICB3_{11}$, $ICB3_{12}$, $ICB3_{13}$, $ICB3_{21}$, $ICB3_{22}$, $ICB3_{23}$, $ICB3_{31}$, $ICB3_{32}$, and $ICB3_{33}$.

Further, the preview image generation unit 72 generates a preview image IPB3 in which the nine candidate images $ICB3_{11}$, $ICB3_{12}$, $ICB3_{13}$, $ICB3_{21}$, $ICB3_{22}$, $ICB3_{23}$, $ICB3_{31}$, $ICB2_{32}$, and $ICB3_{33}$ are two-dimensionally disposed with the third image quality parameter type as a vertical axis and the fourth image quality parameter type as a horizontal axis.

Subsequently, the user uses the input device 50 to select one candidate image among the nine candidate images $ICB3_{11}$, $ICB3_{12}$, $ICB3_{13}$, $ICB3_{21}$, $ICB3_{22}$, $ICB3_{23}$, $ICB3_{31}$, $ICB3_{32}$, and $ICB3_{33}$ of the preview image IPB3. The selection operation reception unit 76 receives the operation of selecting the candidate image.

The image quality parameter value determination unit 78 determines the candidate value of the third image quality parameter type corresponding to the selected candidate image, as a set value of the third image quality parameter type. The set value of the fourth image quality parameter type is not determined at this point.

As described above, assuming that K is an integer for the three or more image quality parameter types acquired according to the imaging site, a preview image in which a plurality of candidate images are disposed for a parameter type set of a (K)-th image quality parameter type and a (K+1)-th image quality parameter type combined in descending order of the priority is displayed, and a set value of the (K)-th image quality parameter type having a higher priority is determined.

Similarly, steps S7 and S8 are executed to determine a set value for the (N)-th parameter type set. For an image quality parameter type having a lowest priority, the medical imaging data need only be subjected to the image processing using a plurality of candidate values of the image quality parameter type to generate a plurality of candidate images, a preview image in which the plurality of candidate images are one-dimensionally disposed need only be generated, and any one of the candidate images need only be selected by the user.

According to the first embodiment, by configuring the second parameter type set with the third image quality parameter type and the fourth image quality parameter type, it is possible to, without examining the first image quality parameter type and the second image quality parameter type of which the set value is already determined, quickly determine the set value of the subsequent image quality parameter type.

On the other hand, according to the second embodiment, by configuring the second parameter type set with the second image quality parameter type and the third image quality parameter type and applying the second image quality parameter type that led to the selection of the candidate image in the first parameter type set to perform evaluation again, it is possible to more detailedly examine the compatibility of the second parameter type with the other image quality parameter type.

The first embodiment and the second embodiment may be appropriately used. For example, among the three or more image quality parameter types, the image quality parameter type having a relatively high priority may be examined in detail to determine the set value as in the second embodiment, and the set value of the image quality parameter type having a relatively low priority may be quickly determined as in the first embodiment.

Third Embodiment

The image quality parameter value determination unit 78 determines the candidate value of the image quality parameter type corresponding to the candidate image selected from the preview image as the set value, and causes the memory 44 (an example of a "storage unit") to hold the determined set value for each image quality parameter type, in the first embodiment and the second embodiment. The set value may be held for each determined doctor, or may be held for each hospital including a plurality of doctors.

Further, in a case where the set values of the respective image quality parameter types for a certain number of patients are accumulated, the preview image generation unit 72 may emphasize the candidate image that is subjected to the image processing using the candidate value that is most frequently selected in each image quality parameter type.

Figure 7:
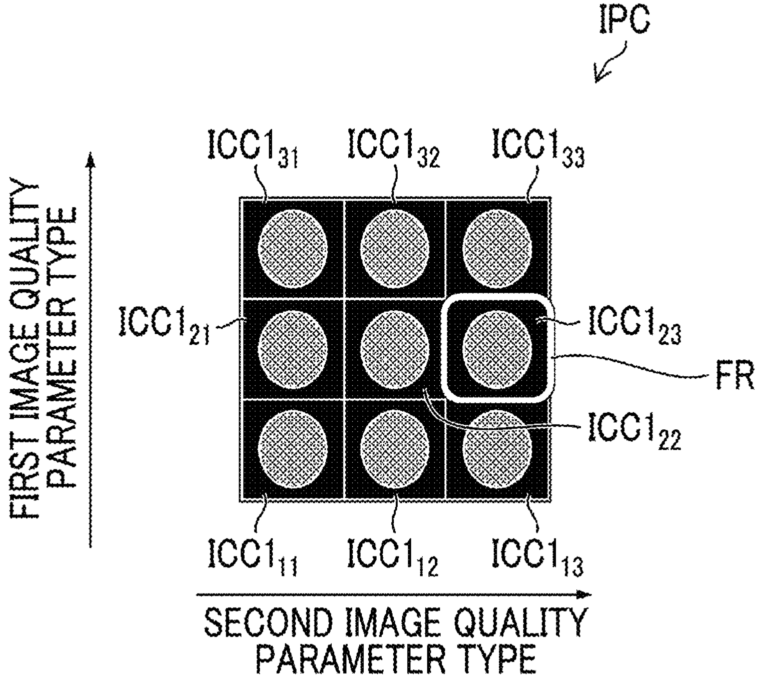
FIG. 7 is a diagram showing an example of a preview image.

FIG. 7 is a diagram showing an example of a preview image according to a third embodiment. Nine candidate images $ICC1_{11}$, $ICC1_{12}$, $ICC1_{13}$, $ICC1_{21}$, $ICC1_{22}$, $ICC1_{23}$, $ICC1_{31}$, $ICC1_{32}$, and $ICC1_{33}$ included in a preview image IPC are images obtained by performing image processing on the medical imaging data for each of combinations of the three candidate values P1A, P1B, and P1C of the first image quality parameter type and the three candidate values P2A, P2B, and P2C of the second image quality parameter type, that is, for each of nine combinations of P1A×P2A, P1A×P2B, P1A×P2C, P1B×P2A, P1B×P2B, P1B×P2C, P1C×P2A, P1C× P2B, and P1C×P2C.

Here, it is assumed that the candidate value most frequently selected for the first image quality parameter type is P1B, and the candidate value most frequently selected for the second image quality parameter type is P2C. In this case, the preview image generation unit 72 relatively emphasizes the candidate image $ICC1_{23}$ (an example of a "first candidate image") that is a combination of P1B×P2C over a candidate image (an example of a "second candidate image") other than the candidate image $ICC1_{23}$. In the preview image IPC shown in FIG. 7, the candidate image $ICC1_{23}$ is emphasized by being surrounded by a frame FR.

As a result, since the candidate value of the image quality parameter type that has been frequently selected in the past is used as guide information, it is possible to easily and intuitively select the candidate image for determining the set value for each image quality parameter type.

The emphasis of the candidate image is not limited to the aspect of being surrounded by the frame FR, and it is sufficient that the user can recognize that the candidate image is emphasized.

Fourth Embodiment

The priority given to the image quality parameter type may be given relatively higher as the image quality parameter type whose setting value varies in preference.

Similarly to the third embodiment, the image quality parameter value determination unit 78 stores the determined set value in the memory 44 for each image quality parameter type. In a case where the set values of the respective image quality parameter types for a certain number of patients are accumulated, the processor 42 reads out the set value determined in the past for each image quality parameter type from the memory 44, and calculates the variation of the set value for each image quality parameter type. Then, the priority is re-given relatively higher to the image quality parameter type of which a variation in the set value is relatively large.

That is, since it is considered that the image quality parameter type having a large variation in the set value is the image quality parameter type having a variation in the preference of the user, a high priority is re-given. On the other hand, since it is considered that the image quality parameter type having a small variation in the set value is the image quality parameter type for which the necessity of the user to select the set value is low, a low priority is re-given. The image quality parameter type having a small variation in the set value may be deleted from among three or more image quality parameter types acquired according to the imaging site. In this case, for the image quality parameter having a small variation in the set value, an average value thereof may be used as a fixed value.

Thereafter, the processor 42 performs the same processing as in the first embodiment and the second embodiment based on the re-given priority.

As described above, the processor 42 performs processing according to the priority given in step S2 until the set values are accumulated from the shipment. Then, in a case where the set values of the respective image quality parameter types for a certain number of patients are accumulated, the image quality parameter types having a variation in the preference are automatically extracted, and the image quality parameter types are given priorities according to the variation in the set values, and rearranged.

For example, it is assumed that the imaging site is "head", and the first priority given to the user is "space resolution", the second priority is "S/N ratio (denoising intensity)", the third priority is "edge emphasis intensity", and the fourth priority is "contrast".

After that, in a case where the variation in the set value of the "edge emphasis intensity" is relatively small as a result of calculating the variation in the set value for each image quality parameter type, the processor 42 relatively lowers the priority of the "edge emphasis intensity". That is, in a case where the imaging site is "head", the re-given first priority is "spatial resolution", the re-given second priority is "S/N ratio (denoising intensity)", the re-given third priority is "contrast", and the re-given fourth priority is "edge emphasis intensity".

In addition, in a case where the variation in the set value of the "edge emphasis intensity" is relatively small, the processor 42 may delete the "edge emphasis intensity" from the image quality parameter type selected according to the imaging site "head". That is, in a case where the imaging site is "head", the re-given first priority may be "space resolution", the re-given second priority may be "S/N ratio (denoising intensity)", and the re-given third priority may be "contrast". In this case, the processor 42 need only perform the processing by setting the average value of the set values with little variation as the fixed value for the "edge emphasis intensity".

According to the fourth embodiment, among the plurality of image quality parameter types, the set value can be preferentially selected from the image quality parameter type of which the preference is likely to vary, that is, the image quality parameter type which is important for the user. As a result, it is possible to assist the user in determining the set value of the image quality parameter type by using a parameter database of a certain number of medical images, such as several hundred cases.

Fifth Embodiment

FIG. 8 is a flowchart showing steps of a medical image processing method according to a fifth embodiment performed by the medical image processing device 40. In the fifth embodiment, each parameter type set includes three image quality parameter types.

The processing of step S11 and step S12 is the same as the processing of step S1 and step S2 of the first embodiment.

In step S13, the preview image display unit 74 generates the preview image of the first parameter type set and displays the preview image on the display device 60.

The first parameter type set includes a first image quality parameter type having a first priority, a second image quality parameter type having a second priority, and a third image quality parameter type having a third priority. Here, it is assumed that the first image quality parameter type has three candidate values P1A, P1B, and P1C, the second image quality parameter type has three candidate values P2A, P2B, and P2C, and the third image quality parameter type has three candidate values P3A, P3B, and P3C.

The preview image generation unit 72 performs image processing on the medical imaging data for each of combinations of the respective candidate values of the first image quality parameter type, the respective candidate values of the second image quality parameter type, and the respective candidate values of the third image quality parameter type, that is, for each of 27 combinations of P1A×P2A×P3A, P1A×P2A×P3B, P1A×P2A×P3C, P1A×P2B×P3A, P1A×P2B×P3B, P1A×P2B×P3C, P1A×P2C×P3A, P1A×P2C×P3B, P1A×P2C×P3C, P1B×P2A×P3A, P1B×P2A×P3B, P1B×P2A×P3C, P1B×P2B×P3A, P1B×P2B×P3B, P1B×P2B×P3C, P1B×P2C×P3A, P1B×P2C×P3B, P1B×P2C×P3C, P1C×P2A×P3A, P1C×P2Ax P3B, P1C×P2Ax P3C, P1C×P2B×P3A, P1C×P2B×P3B, P1C×P2B×P3C, P1C×P2C×P3A, P1C×P2C×P3B, and P1C×P2C×P3C, to generate 27 types of candidate images $ICD1_{111}$, $ICD1_{112}$, $ICD1_{113}$, $ICD1_{121}$, $ICD1_{122}$, $ICD1_{123}$, $ICD1_{131}$, $ICD1_{132}$, $ICD1_{133}$, $ICD1_{211}$, $ICD1_{212}$, $ICD1_{213}$, $ICD1_{221}$, $ICD1_{222}$, $ICD1_{223}$, $ICD1_{231}$, $ICD1_{232}$, $ICD1_{233}$, $ICD1_{311}$, $ICD1_{312}$, $ICD1_{313}$, $ICD1_{321}$, $ICD1_{322}$, $ICD1_{323}$, $ICD1_{331}$, $ICD1_{332}$, and $ICD1_{333}$.

Further, the preview image generation unit 72 generates the preview image for each value of the third image quality parameter type from among the 27 types of candidate images.

Here, the preview image generation unit 72 generates a preview image IPD11 (an example of a "first preview image") in which, among the 27 types of candidate images, the nine types of candidate images $ICD1_{111}$, $ICD1_{121}$, $ICD1_{131}$, $ICD1_{211}$, $ICD1_{221}$, $ICD1_{231}$, $ICD1_{311}$, $ICD1_{321}$, and $ICD1_{331}$ in which the candidate value of the third image quality parameter type is P3A (an example of a "first candidate value") are two-dimensionally disposed with the first image quality parameter type as a vertical axis and the second image quality parameter type as a horizontal axis.

In addition, the preview image generation unit 72 generates a preview image IPD12 (an example of a "second preview image") in which, among the 27 types of candidate images, the nine types of candidate images $ICD1_{112}$, $ICD1_{122}$, $ICD1_{132}$, $ICD1_{212}$, $ICD1_{222}$, $ICD1_{232}$, $ICD1_{312}$, $ICD1_{322}$, and $ICD1_{332}$ in which the candidate value of the third image quality parameter type is P3B (an example of a "second candidate value") are two-dimensionally disposed with the first image quality parameter type as a vertical axis and the second image quality parameter type as a horizontal axis.

Similarly, the preview image generation unit 72 generates a preview image IPD13 in which, among the 27 types of candidate images, the nine types of candidate images $ICD1_{113}$, $ICD1_{123}$, $ICD1_{133}$, $ICD1_{213}$, $ICD1_{223}$, $ICD1_{233}$, $ICD1_{313}$, $ICD1_{323}$, and $ICD1_{333}$ in which the candidate value of the third image quality parameter type is P3C are two-dimensionally disposed with the first image quality parameter type as a vertical axis and the second image quality parameter type as a horizontal axis.

Figure 9:
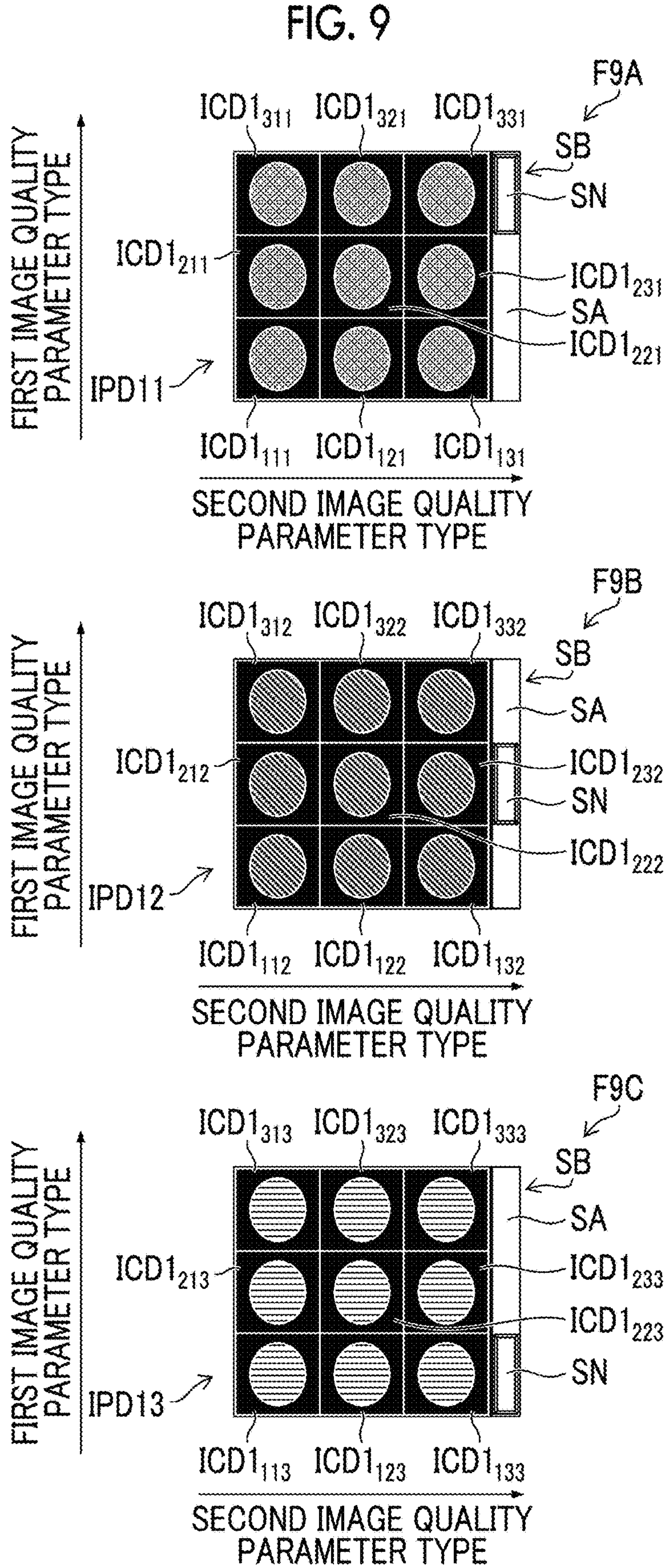
FIG. 9 is a diagram showing an example of a preview image.

FIG. 9 is a diagram showing an example of a preview image displayed on the display device 60. F9A in FIG. 9 shows the preview image IPD11. In addition, a scroll bar SB is displayed on a right side of the preview image IPD11. The scroll bar SB includes a scroll area SA that extends linearly in an up-down direction, and a scroll knob SN that is movable in the up-down direction in the scroll area SA.

In the state shown in F9A, the scroll bar SB is located at an upper part in the scroll area SA. Here, the position of the scroll bar SB in the scroll area SA corresponds to the candidate value of the third image quality parameter type. The user can move the scroll bar SB in the scroll area SA by using the input device 50.

In a case where the user moves the scroll bar SB to a central part of the scroll area SA (an example of a "switching operation"), the preview image display unit 74 displays the preview image IPD12, which is the preview image of the first parameter type set and of which the candidate value of the third image quality parameter type is P3B, on the display device 60. F9B in FIG. 9 shows the preview image IPD12.

In addition, in a case where the user moves the scroll bar SB to a lower part of the scroll area SA, the preview image display unit 74 displays the preview image IPD13, which is the preview image of the first parameter type set and of which the candidate value of the third image quality parameter type is P3C, on the display device 60. F9C in FIG. 9 shows the preview image IPD13.

In step S14, the user operates the scroll bar SB to display and select any one of the preview image IPD11, the preview image IPD12, or the preview image IPD13 on the display device 16. The selection operation reception unit 76 receives the operation of selecting the preview image. The action of the user corresponds to the selection of the candidate value of the third image quality parameter type.

In step S15, the user uses the input device 50 to select one candidate image from among the preview images displayed on the display device 16. The selection operation reception unit 76 receives the operation of selecting the candidate image.

That is, in a case where the preview image IPD11 is displayed, the user selects one candidate image among the nine types of candidate images $ICD1_{111}$, $ICD1_{121}$, $ICD1_{131}$, $ICD1_{211}$, $ICD1_{221}$, $ICD1_{231}$, $ICD1_{311}$, $ICD1_{321}$, and $ICD1_{331}$. In a case where the preview image IPD12 is displayed, the user selects one candidate image among the nine types of candidate images $ICD1_{112}$, $ICD1_{122}$, $ICD1_{132}$, $ICD1_{212}$, $ICD1_{222}$, $ICD1_{232}$, $ICD1_{312}$, $ICD1_{322}$, and $ICD1_{332}$. In a case where the preview image IPD13 is displayed, the user selects one candidate image among the nine types of candidate images $ICD1_{113}$, $ICD1_{123}$, $ICD1_{133}$, $ICD1_{213}$, $ICD1_{223}$, $ICD1_{233}$, $ICD1_{313}$, $ICD1_{323}$, and $ICD1_{333}$. The action of the user corresponds to the selection of the candidate value of the first image quality parameter type and the candidate value of the second image quality parameter type.

The image quality parameter value determination unit 78 determines the candidate value of the third image quality parameter type corresponding to the preview image selected in step S14, and the candidate value of the first image quality parameter type and the candidate value of the second image quality parameter type corresponding to the candidate image selected in step S15, as the set values of the respective image quality parameter types.

Subsequently, in step S16, the preview image display unit 74 generates a plurality of preview images of the second parameter type set and displays any one preview image on the display device 60. The second parameter type set includes a fourth image quality parameter type having a fourth priority, a fifth image quality parameter type having a fifth priority, and a sixth image quality parameter type having a sixth priority.

In step S17, the user uses the input device 50 to select one preview image from the plurality of preview images of the second parameter type set. The selection operation reception unit 76 receives the operation of selecting the preview image.

In step S18, the user uses the input device 50 to select one candidate image from the preview image selected in step S17. The selection operation reception unit 76 receives the operation of selecting the candidate image. As a result, the set value is determined for the second parameter type set.

Similarly, steps S19, S20, and S21 are executed to determine the set value for the (N)-th parameter type set.

Finally, in step S22, the final image generation unit 80 performs image processing on the acquired medical imaging data by applying the determined set value of each image quality parameter type, to generate a medical image that is a final image.

According to the fifth embodiment, it is possible to determine the parameter in a shorter time than in a case of determining two set values at a time as in the first embodiment, in a case of determining the set values of the large number of image quality parameter types.

The method of determining the set values in the image quality parameter value determination unit 78 is not limited to an example of determining three set values at a time. For example, the image quality parameter value determination unit 78 may determine the candidate value of the first image quality parameter type corresponding to the candidate image selected in step S4 as the set value of the first image quality parameter type, and may not determine the set value for the second image quality parameter type and the third image quality parameter type.

In this case, the second parameter type set in step S5 includes a second image quality parameter type, a third image quality parameter type, and a fourth image quality parameter type having a fourth priority. Similarly to the second embodiment, a range of the plurality of candidate values of the second image quality parameter type of the second parameter type set is relatively narrower than a range of the plurality of candidate values of the second image quality parameter type of the first parameter type set. In addition, the range of the plurality of candidate values of the second image quality parameter type of the second parameter type set includes the set value of the second image quality parameter type of the first parameter type set. The same applies to the range of the candidate value of the third image quality parameter type.

In addition, the image quality parameter value determination unit 78 may determine the candidate value of the first image quality parameter type and the candidate value of the second image quality parameter type corresponding to the candidate image selected in step S4, as the set value of the first image quality parameter type and the set value of the second image quality parameter type, respectively, and may not determine the set value for the third image quality parameter type.

In this case, the second parameter type set in step S5 includes a third image quality parameter type, a fourth image quality parameter type having a fourth priority, and a fifth image quality parameter type having a fifth priority. Similarly to the second embodiment, a range of the plurality of candidate values of the third image quality parameter type of the second parameter type set is relatively narrower than a range of the plurality of candidate values of the third image quality parameter type of the first parameter type set. In addition, the range of the plurality of candidate values of the third image quality parameter type of the second parameter type set includes the set value of the third image quality parameter type of the first parameter type set.

Figure 10:
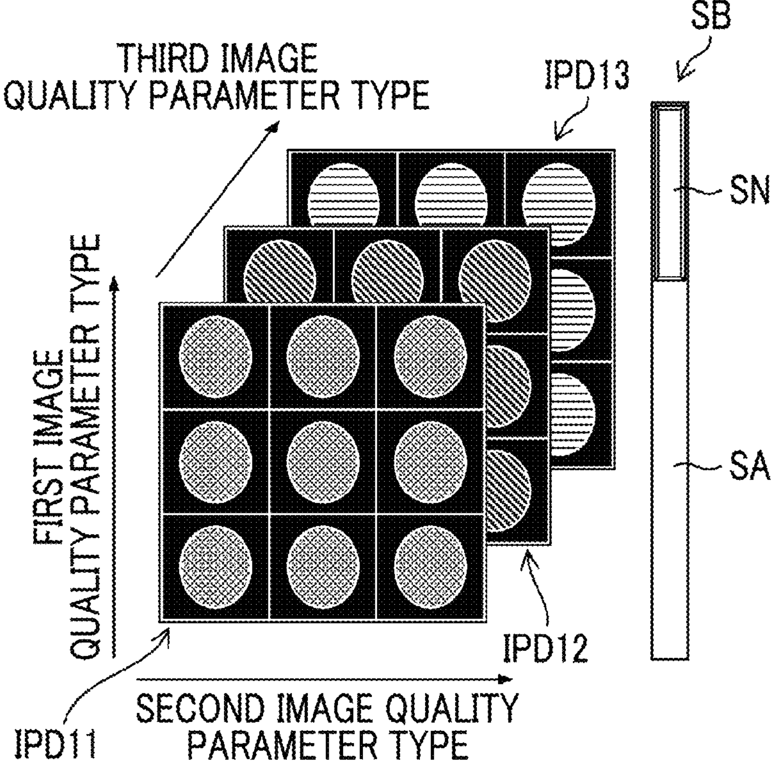
FIG. 10 is a diagram showing an example of a preview image.

In addition, the position of the scroll bar SB is not limited to a position adjacent to the preview image. FIG. 10 is a diagram showing an example of a preview image in which the scroll bar is disposed at a different position. As shown in FIG. 10, the scroll bar need only be disposed in a screen of the display device 60. In addition, the scroll bar SB may include a scroll area SA that extends linearly in a left-right direction and a scroll knob SN that is movable in the left-right direction in the scroll area SA.

Further, a preview image other than the preview image corresponding to the position of the scroll bar SB may be displayed. The preview image other than the preview image corresponding to the position of the scroll bar SB may be displayed such that a part thereof is hidden behind the preview image corresponding to the position of the scroll bar SB. In the example shown in FIG. 10, the preview image corresponding to the position of the scroll bar SB is the preview image IPD11, and the other preview images IPD12 and IPD13 are displayed to be partially hidden behind the preview image IPD11. Through the display in this way, the user can recognize the presence of the preview image other than the preview image corresponding to the position of the scroll bar SB.

Figure 11:
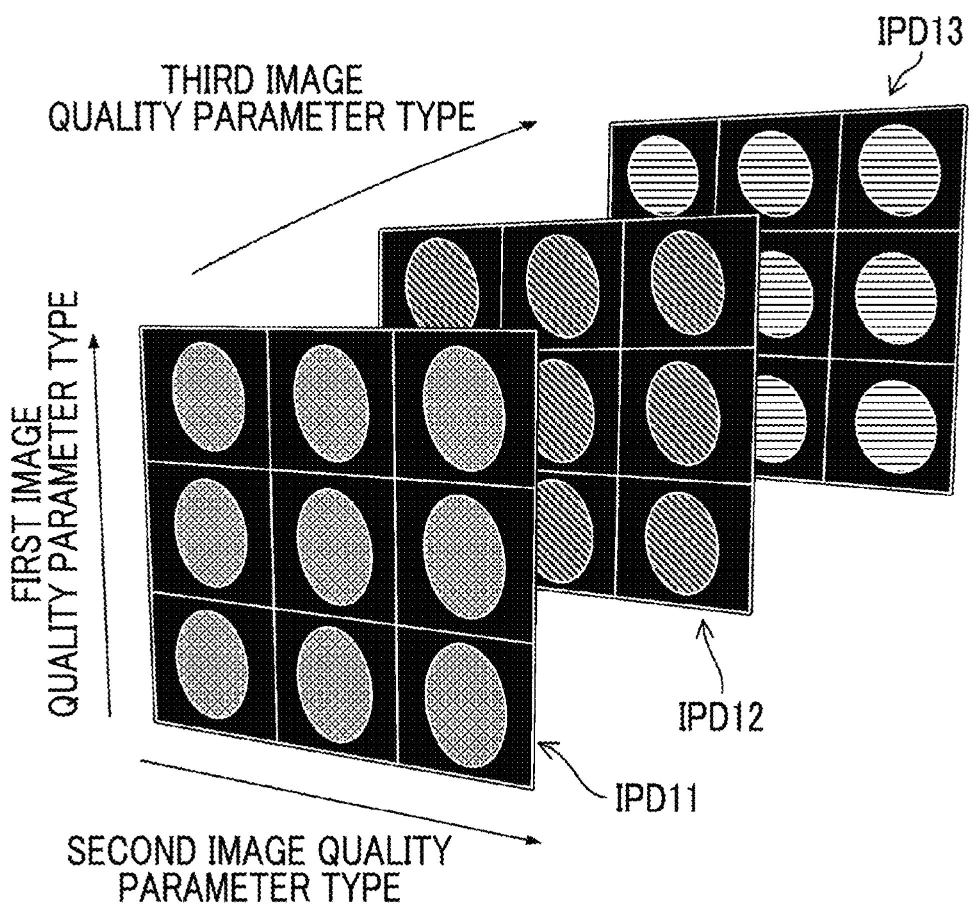
FIG. 11 is a diagram showing an example of a preview image.

In addition, the switching of the preview image is not limited to using a scroll bar. FIG. 11 is a diagram showing an example of a preview image that can be switched using a method different from the scroll bar. As shown in FIG. 11, the preview images may be displayed as being disposed in a space with a depth (so-called 3D flip display). The user can select a desired preview image by operating the input device 50. In addition, the first preview image may be switched by operating the input device 50.

Sixth Embodiment

In a case where the candidate image is a three-dimensional image and the image included in the preview image is a slice image of the candidate image, the slice position may be switched by using a scroll bar.

FIG. 12 is a diagram showing an example of a preview image displayed on the display device 60. Each candidate image included in a preview image IPE1 (an example of a "third preview image") shown in F12A of FIG. 12 is a slice image at the same slice position (an example of a "first slice position") in the same direction. As shown in F12A, the scroll bar SB is displayed on a right side of the preview image IPE1. Here, the position of the scroll bar SB in the scroll area SA corresponds to the slice position of the candidate image. The user can move the scroll bar SB in the scroll area SA by using the input device 50.

In a case where the user moves the scroll bar SB (an example of a "switching operation"), the preview image display unit 74 displays a preview image IPE2 different from the preview image IPE1. F12B in FIG. 12 shows the preview image IPE2 (an example of a "fourth preview image"). The slice position (an example of a "second slice position") of each candidate image of the preview image IPE2 is a position different from the slice position of each candidate image of the preview image IPE1.

The selection operation reception unit 76 receives the operation of selecting one candidate image from the preview image IPE1 or the preview image IPE2.

According to the sixth embodiment, since the preview images of the slice images at the different slice positions can be displayed, the user can select an appropriate value for each image quality parameter type. A switching button or the like for changing the slice direction may be displayed together with the preview image.

Others

The medical image processing device, the medical image processing method, the program, and the image diagnostic system according to the present disclosure can also be applied to an image processing device, an image processing method, a program, and an image diagnostic system that use a natural image other than the medical image. For example, it can be applied to a technique of performing an inspection of detecting a defective portion such as fissuring from imaging data of a social infrastructure facility, such as transportation, electricity, gas, and water supply.

The technical scope of the present invention is not limited to the scope described in the above embodiments. The configurations and the like in each embodiment can be appropriately combined between the respective embodiments without departing from the spirit of the present invention.

EXPLANATION OF REFERENCES

10: image diagnostic system
20: image diagnostic apparatus
30: information processing apparatus
40: medical image processing device
42: processor
44: memory
50: input device
60: display device

What is claimed is:

1. A medical image processing device comprising:
at least one processor; and
at least one memory that stores a command to be executed by the processor,
wherein the processor
acquires medical imaging data, displays, on a display device, a preview image in which, for a parameter type set of two image quality parameter types among three or more image quality parameter types related to an image quality of a medical image generated from the medical imaging data, a plurality of candidate images obtained by performing image processing on the medical imaging data by respectively combining a plurality of different candidate values of one image quality parameter type and a plurality of different candidate values of the other image quality parameter type are two-dimensionally disposed with the one image quality parameter type as one axis and the other image quality parameter type as the other axis, receives an operation of selecting one candidate image from the preview image, and determines at least one of the candidate value of the one image quality parameter type or the candidate value of the other image quality parameter type corresponding to the selected candidate image, as a set value of the image quality parameter type, the three or more image quality parameter types are each given a priority, after the set value is determined for a first parameter type set including a first image quality parameter type having a first priority and a second image quality parameter type having a second priority, the set value is determined for a second parameter type set different from the first parameter type set, and image processing is performed on the medical imaging data by applying the set value of each of the three or more image quality parameter types, to generate a medical image.

2. The medical image processing device according to claim 1, wherein the processor determines the set value of the first image quality parameter type and the set value of the second image quality parameter type for the first parameter type set, and the second parameter type set includes a third image quality parameter type having a third priority and a fourth image quality parameter type having a fourth priority.

3. The medical image processing device according to claim 1, wherein the processor determines the set value of the first image quality parameter type for the first parameter type set, and the second parameter type set includes the second image quality parameter type and a third image quality parameter type having a third priority.

4. The medical image processing device according to claim 3, wherein a range of the plurality of candidate values of the second image quality parameter type of the second parameter type set is relatively narrower than a range of the plurality of candidate values of the second image quality parameter type of the first parameter type set, and includes the candidate value of the second image quality parameter type corresponding to the selected candidate image of the first parameter type set.

5. The medical image processing device according to claim 1, further comprising:

a storage that holds the set values, which are determined in the past, of the three or more image quality parameter types, wherein the processor relatively emphasizes a first candidate image corresponding to a combination of the set value, which is determined most frequently in the past, of the one image quality parameter type and the set value, which is determined most frequently in the past, of the other image quality parameter type over a second candidate image different from the first candidate image, in the preview image.

6. The medical image processing device according to claim 1, wherein the processor acquires an imaging site of the medical imaging data, and acquires the three or more image quality parameter types according to the imaging site.

7. The medical image processing device according to claim 1, wherein the priority is given relatively higher to the image quality parameter type of which a variation in the set value determined in the past is relatively large.

8. The medical image processing device according to claim 1, wherein the first parameter type set further includes a third image quality parameter type having a third priority, and the processor displays, on the display device, a first preview image in which the plurality of candidate images having a first candidate value of the third image quality parameter type are two-dimensionally disposed among a plurality of candidate images obtained by performing image processing on the medical imaging data by respectively combining a plurality of different candidate values of the first image quality parameter type, a plurality of different candidate values of the second image quality parameter type, and a plurality of different candidate values of the third image quality parameter type, receives a switching operation for switching the candidate values of the third image quality parameter type, displays a second preview image in which the plurality of candidate images having a second candidate value, which is different from the first candidate value, of the third image quality parameter type are two-dimensionally disposed in accordance with the switching operation, receives an operation of selecting one candidate image from the first preview image or the second preview image, and determines at least the candidate value of the first image quality parameter type corresponding to the selected candidate image, as a set value of the first image quality parameter type.

9. The medical image processing device according to claim 8, wherein the processor determines the candidate value of the second image quality parameter type corresponding to the selected candidate image as a set value of the second image quality parameter type, and determines the candidate value of the third image quality parameter type corresponding to the selected candidate image, as a set value of the third image quality parameter type.

10. The medical image processing device according to claim 1, wherein the candidate image is a three-dimensional image, and the processor displays a third preview image in which slice images at first slice positions of the plurality of candidate images are two-dimensionally disposed, receives a switching operation for switching slice positions of the plurality of candidate images, displays a fourth preview image in which slice images at second slice positions different from the first slice positions are two-dimensionally disposed in accordance with the switching operation, and receives an operation of selecting one candidate image from the third preview image or the fourth preview image.

11. The medical image processing device according to claim 1, wherein the processor performs image processing on the medical imaging data by applying the set value determined for the first parameter type set, to generate a plurality of candidate images of the second parameter type set.

12. An image diagnostic system comprising:

the medical image processing device according to claim 1;

an image diagnostic apparatus that images the medical imaging data;

the display device; and an input device for a user to perform an operation of selecting one candidate image from the preview image.

13. The image diagnostic system according to claim 12, wherein the image diagnostic apparatus is a magnetic resonance imaging (MRI) apparatus.

14. A medical image processing method comprising:

via at least one processor, acquiring medical imaging data;

displaying, on a display device, a preview image in which, for a parameter type set of two image quality parameter types among three or more image quality parameter types related to an image quality of a medical image generated from the medical imaging data, a plurality of candidate images obtained by performing image processing on the medical imaging data by respectively combining a plurality of different candidate values of one image quality parameter type and a plurality of different candidate values of the other image quality parameter type are two-dimensionally disposed with the one image quality parameter type as one axis and the other image quality parameter type as the other axis;

receiving an operation of selecting one candidate image from the preview image; and determining at least one of the candidate value of the one image quality parameter type or the candidate value of the other image quality parameter type corresponding to the selected candidate image, as a set value of the image quality parameter type, wherein the three or more image quality parameter types are each given a priority, after the set value is determined for a first parameter type set including a first image quality parameter type having a first priority and a second image quality parameter type having a second priority, the set value is determined for a second parameter type set different from the first parameter type set, and image processing is performed on the medical imaging data by applying the set value of each of the three or more image quality parameter types, to generate a medical image.

15. A non-transitory, computer-readable tangible recording medium which records thereon a program for causing, when read by a computer, a processor provided to the computer to execute the medical image processing method according to claim 14.

* * * * *